(12) United States Patent
Pegoraro et al.

(10) Patent No.: US 7,276,606 B2
(45) Date of Patent: Oct. 2, 2007

(54) PHENANTRIDINE ANALOGUES AND USES THEREOF

(75) Inventors: Stefano Pegoraro, Planegg (DE); Martin Lang, Graefelfing (DE); Juliane Feurle, Munich (DE); Juergen Kraus, Starnberg (DE)

(73) Assignee: 4SC AG, Martinsried (DE)

(*) Notice: Subject to any disclaimer, the term of this patent is extended or adjusted under 35 U.S.C. 154(b) by 37 days.

(21) Appl. No.: 11/118,421

(22) Filed: May 2, 2005

(65) Prior Publication Data
US 2005/0282801 A1 Dec. 22, 2005

Related U.S. Application Data

(60) Provisional application No. 60/566,820, filed on Apr. 30, 2004.

(51) Int. Cl.
C07D 221/12 (2006.01)
(52) U.S. Cl. .................................... 546/108
(58) Field of Classification Search ................ 546/108
See application file for complete search history.

(56) References Cited

U.S. PATENT DOCUMENTS 3,661,914 A 5/1972 Van De Burg

FOREIGN PATENT DOCUMENTS

| SU | 365 357 | 1/1973 |
|----|---------|--------|
| WO | WO 02/20463 A | 3/2002 |
| WO | WO 01/42219 A | 6/2004 |

OTHER PUBLICATIONS

Sheinkman et al., (Khimiya Geterotsiklicheskikh Soedinenii 1972, 5 669-72, list of compounds in Table).*
Baudoin, O. et al.: J. Chem. Org. vol. 67, No. 4, 2002, —1199 p. 1207, XP002300783.
Goerlitzer K. et al.: Pharmzie, vol. 57, No. 6, 2002, pp. 362-373, XP001183919.
Goerlitzer K. et al.: Pharmzie, vol. 52, No. 8, 1997, pp. 575-578, XP001183918.
Goerlitzer K. et al.: Pharmzie, vol. 51, No. 4, 1996, pp. 207-212, XP001183917.
Hammond M. et al.: Bioorg. Med, Hem. Lett., vol. 13, No. 12, 2003, pp. 1989-1992, XP002271705.
Dow R. et al.: J. Med. Chem. vol. 37 No. 14, 1994, pp. 2224-2231, XP002300784.
Von Dobeneck, et al.: Chem. Ber., vol. 95, 1962, pp. 1484-1492, XP009037705.
Bowman W. R. et al.: Tetrahedron, vol. 47, No. 48, 1991, pp. 10119-10128, XP002300785.
Sheinkman, A. K. et al.: "Reactions of cyclammonlum cations. XVIII. Interaction of N-acylphenanthridinium salts in situ with nucleophilic aromatic and heteroaromatic compounds" Khimiya Geterotsiklicheskikh Soedinenii (5), 669-72 Coden: KGSSAQ; ISSN: 0132-6244, 1972, XP009038123.
Van Riezen, Henk et al.: "0I 77, a new tricyclic antidepressant" Arzeneimittel-Forschung, 23(9), 1595-302 Coden: Arznad; ISSN: 0004-4172, 1973, XP009038141.
International Search Report dated Jan. 2004.

* cited by examiner

Primary Examiner—D. Margaret Seaman
Assistant Examiner—Nizal S. Chandrakumar
(74) Attorney, Agent, or Firm—Millen, White, Zelano & Branigan PC

(57) ABSTRACT

The present invention relates to compounds of the general formula (IV) and (II) and salts and physiologically functional derivatives thereof,

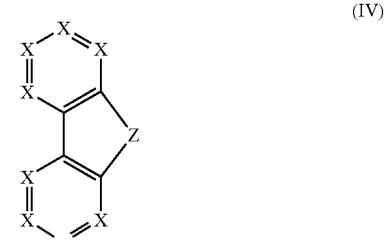

(IV)

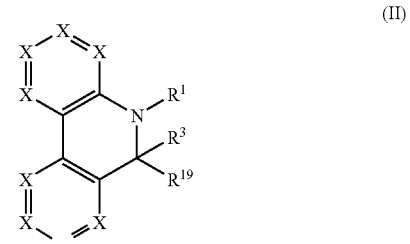

(II)

wherein
X is C—$R^8$ or N; and
Z is independently one of the following groups:

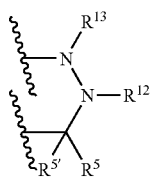 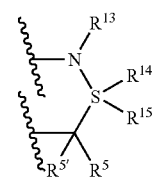 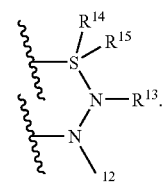

15 Claims, No Drawings

PHENANTRIDINE ANALOGUES AND USES THEREOF

This application claims the benefit of the filing date of U.S. Provisional Application Ser. No. 60/566,820 filed Apr. 30, 2004, which is incorporated by reference herein.

The present invention relates to compounds of the general formula (I), formula (II), formula (III) and formula (IV) or a salt or a physiologically functional derivative or a stereoisomer thereof, for use as a medicament. Furthermore, the present invention relates to compounds of the general formula (II) and formula (IV) or a salt or a physiologically functional derivative or a stereoisomer thereof. The compounds of the invention are exceptionally useful for the treatment of diseases associated with abnormal and hyperproliferation of cells in a mammal, especially humans. In particular, they are useful for the treatment of diseases characterized by a hyperproliferation of T cells and/or keratinocytes.

Diseases which are characterized by hyperproliferation of keratinocytes within the meaning of the present invention are diseases wherein patients exhibit locally or over the whole body a thickened epidermis in comparison to healthy epidermis. A thickened epidermis is deemed to be an epidermis, which is thickened in comparison to healthy skin by at least about 10%, preferably about 30%, in particular about 50% and most preferably about 80%. Methods for measuring thickness of epidermis are known to someone skilled in the art. Wetzel et al. (Arch. Dermatol. Res., April 2003) describe, for example, optical coherence tomography and Baulieu et al. (Proc. Natl. Acad. Sci. USA, 2000, 97:4279-4284), skin echographic measurement, which both represent non-invasive methods for the measurement of the thickness of the epidermis. Furthermore the thickness of the epidermis can be determined histologically in section of skin biopsies as described in, for example, El-Domyati et al., (Exp. Dermatol., 2002; 11:398-405) or Schopf et al. (J. Am. Acad. Dermatol. 2002; 46:886-91). Since the epidermis exhibits different thickness in different regions of the skin it is necessary for a comparison of the thickness of healthy and diseased epidermis to compare the respective thickness of the epidermis in similar regions of the skin. Furthermore there is a certain variation of the thickness of the epidermis within the same regions of the skin among two individuals. It is therefore preferred that the thickness of the epidermis is measured, for example, at the left and at the right leg of a diseased individual under the precondition that not the complete skin is affected by the disease. In general diseases characterized by hyperproliferation of keratinocytes are accompanied by a reddening of the effected region of the skin such that someone skilled in the art can distinguish diseased regions of the skin of the patients from healthy regions of the skin solely based on the reddening. The thickening of epidermis in diseases characterized by hyperproliferation of keratinocytes can occur, for example, only locally or can already be detectable, as in psoriasis, in the skin of psoriasis patients which is not discernibly effected based on a reddening and a lesion, respectively. In psoriasis patients a further thickening of the epidermis is, however, also detectable in effected areas of the skin (=lesion). Examples of diseases, which are characterized by hyperproliferation of keratinocytes within the meaning of the present invention are psoriasis, in particular psoriasis vulgaris, psoriasis capitis, psoriasis guttata, psoriasis inversa, atopic dermatitis, actinic keratosis, hyperkeratosis with epidermolytic hyperkeratosis and hyperkeratosis lenticularis perstans as well as keratosis pilaris, acne, abnormal scarring, keloids and ichthyoses. Particularly preferred diseases within the meaning of the present invention are atopic dermatitis and psoriasis, in particular psoriasis.

Epidermis is primarily formed from keratinocytes which slowly migrate from basal membrane to the exterior. During this process they pass from a proliferating into a differentiated status to finally die off. Then the dead keratinocytes form the subcorneous at the surface of the skin, which constantly sheds dead cells. By this process a constant regeneration of the skin is achieved. In diseases, which are characterized by hyperproliferation of keratinocytes the balance between differentiation and proliferation of keratinocytes is tilted towards proliferation whereby the epidermis, which comprises more keratinocytes, in particular proliferating keratinocytes is significantly thickened. In such diseases distorted barrier functions are also often found whereby superantigens or pathogens can penetrate the skin more easily. Often an increased inflammation is also observed as e.g. with atopic dermatitis and psoriasis which is then accompanied by the reddening of the skin already mentioned.

Surprisingly it has been observed within the context of the present invention that the compounds of the general formula (I) (II), (III) and (IV) or a salt or a physiologically functional derivative or a stereoisomer thereof, have an inhibiting effect on the hyperproliferation of T cells and/or keratinocytes. This effect increases on one hand the effectiveness of the compounds of the invention for diseases wherein the disease pattern is characterized both by a hyperproliferation of keratinocytes and a hyperproliferation of T cells and on the other hand opens up the possibility to apply the compounds for diseases which are primarily characterized by hyperproliferation of T cells or hyperproliferation of keratinocytes.

Diseases characterized by hyperproliferation of T cells within the meaning of the present invention are diseases in which the patients locally or over the whole body exhibit an increased number of proliferating T cells in comparison to healthy regions of the body. The number of proliferating T cells is deemed increased, if the region of the body in the particular region of the skin examined comprises at least about 10% preferably at least about 30%, in particular about 50% more preferably 100%, most preferably 200% or more proliferating T cells. The term "region of the body" as used herein can comprise any region and organ, respectively, like, e.g. skin, hematopoietic system and lymph nodes.

The term "skin" comprises epidermis, dermis and subcutis, however, in particular the epidermis. The number of proliferating T cells can be determined by a variety of methods known in the prior art. The number of T cells in S or $G_2$ phase can be determined by, e.g. histological staining of a skin punch biopsy or a single cell suspension obtained from a skin punch biopsy can be examined by FACS analysis for the cell cycle phases of the cells.

Examples of skin diseases that are characterized by hyperproliferation of T cells within the meaning of the present invention are psoriasis, atopic dermatitis, alopecia greata, alopecia totalis, alopecia subtotalis, alopecia universalis, alopecia diffusa, atopic dermatitis, lupus erythematodes of the skin, lichen planus, dermatomyositis of the skin, atopic eczema, morphea, scleroderma, psoriasis vulgaris, psoriasis capitis, psoriasis guttata, psoriasis inversa, alopecia greata Ophiasis type, androgenic alopecia, allergic contact dermatitis, irritative contact dermatitis, contact dermatitis, pemphigus vulgaris, pemphigus foliaceus, pemphigus vegetans, scarring mucous membrane pemphigoid, bullous pemphigoid, mucous membrane pemphigoid, dermatitis, dermatitis herpetiformis Duhring, urticaria, necrobiosis lipoidica, erythema nodosum, lichen vidal, prurigo simplex, prurigo nodularis, prurigo acuta, linear IgA dermatosis, polymorphic light dermatosis, erythema solaris, lichen sclerosus et atrophicans, exanthema of the skin, drug exanthema, purpura chronica progressiva, dihidrotic eczema, eczema, fixed drug exanthema, photoallergic skin reaction, lichen simplex periorale dermatitis, rosacea vitiligo, and graft-versus-host-disease.

In particular psoriasis and atopic dermatitis are diseases which are both characterized by hyperproliferation of a keratinocytes and of T cells and the compounds of the present invention are therefore particularly suitable for the therapy thereof since they attack the diseases by at least two different modes of action.

Presently only unsatisfactory therapies for the treatment of these diseases exist, which are often only effective in patient subpopulations and existing therapies as topic or systemic application of corticosteriods or cyclosporine in the case of atopic dermatitis or psoriasis are often accompanied by severe adverse effects. There is, therefore, a necessity for new medicaments preferably without adverse effects for the therapy of these diseases.

The present invention relates to compounds of the general formula (I) or a salt or a physiologically functional derivative or a stereoisomer thereof,

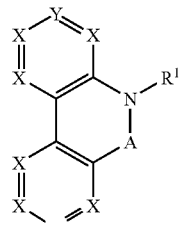

(I)

wherein

A is —C(R$^3$)(R$^4$)—, or if R$^1$ is independently COR$^2$, CO$_2$R$^2$, SOR$^2$, SO$_2$R$^2$, or SO$_3$R$^2$, then A is independently —SO$_2$— or —C(R$^3$)(R$^4$)—;

X is C—R$^8$ or N;

Y is C—R$^9$ or N;

R$^1$ is independently COR$^2$, CO$_2$R$^2$, COCO$_2$R$^2$, SOR$^2$, SO$_2$R$^2$, SO$_3$R$^2$, alkyl, cycloalkyl, alkoxy, —OH, —SH, alkylthio, hydroxyalkyl, haloalkyl, haloalkyloxy, aryl or heteroaryl;

R$^2$ is independently H, alkyl, cycloalkyl, —NH$_2$, alkylamine, aryl or heteroaryl;

R$^3$ is independently H, COR$^2$, CO$_2$R$^2$, SOR$^2$, SO$_2$R$^2$, SO$_3$R$^2$, alkyl, cycloalkyl, alkoxy, alkylamine, —NR$^{11}$COR$^2$, —OH, —SH, alkylthio, hydroxyalkyl, haloalkyl, haloalkyloxy, aryl or heteroaryl, R$^4$ is independently COR$^2$, CO$_2$R$^2$, SOR$^2$, SO$_2$R$^2$, SO$_3$R$^2$, alkyl, cycloalkyl, alkoxy, alkylamine, —NR$^{11}$COR$^2$, —OH, —SH, alkylthio, hydroxyalkyl, haloalkyl, haloalkyloxy, aryl or heteroaryl;

or R$^3$ is absent and R$^4$ is S forming a double bond with the carbon atom of the ring system to which it is attached, or if R$^3$ is absent and R$^4$ is O forming a double bond with the carbon atom of the ring system to which it is attached, then R$^1$ is independently COR$^2$, CO$_2$R$^2$, SOR$^2$, SO$_2$R$^2$ or SO$_3$R$^2$;

R$^8$ is independently H, COR$^2$, CO$_2$R$^2$, SOR$^2$, SO$_2$R$^2$, SO$_3$R$^2$, alkyl, cycloalkyl, alkoxy, —NH$_2$, alkylamine, —NR$^{11}$COR$^2$, halogen, —OH, —SH, alkylthio, hydroxyalkyl, haloalkyl, haloalkyloxy, aryl or heteroaryl;

R$^9$ is independently H, COR$^2$, CO$_2$R$^2$, SOR$^2$, SO$_2$R$^2$, SO$_3$R$^2$, alkyl, cycloalkyl, alkoxy, halogen, —OH, —SH, alkylthio, hydroxyalkyl, haloalkyl, haloalkyloxy, aryl or heteroaryl;

R$^{11}$ is independently H, alkyl, cycloalkyl, alkoxy, —OH, —SH, alkylthio, hydroxyalkyl, aryl, or heteroaryl;

for the use as a medicament.

The present invention also relates to compounds of the general formula (II) or a salt or a physiologically functional derivative or a stereoisomer thereof,

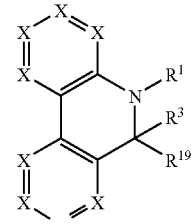

(II)

wherein

X is C—R$^8$ or N;

R$^1$ is independently COR$^{2'}$, CO$_2$R$^2$, COCO$_2$R$^2$, SOR$^2$, SO$_2$R, SO$_3$R$^2$, C$_2$-C$_6$-alkyl, cycloalkyl, alkoxy, —OH, —SH, alkylamine, alkylthio, hydroxyalkyl, haloalkyl, haloalkyloxy, aryl or heteroaryl;

R$^2$ is independently H, alkyl, cycloalkyl, —NH$_2$, alkylamine, aryl or heteroaryl;

R$^{2'}$ is independently C$_2$-C$_6$-alkyl, alkylamine, heteroaryl, or an aromatic group having five, or seven to fifteen carbon atoms, which can optionally be substituted by one or more substituents R', or a phenyl group substituted by one or more substituents R''', or a non-aromatic ring system containing three to eight carbon atoms, wherein one or more of the carbon atoms in the ring can be substituted by a group E, E being defined as S, O, NR', SO, SO$_2$;

R$^3$ is independently H, COR$^2$, CO$_2$R$^2$, SOR$^2$, SO$_2$R$^2$, SO$_3$R$^2$, alkyl, cycloalkyl, alkoxy, alkylamine, —OH, —SH, alkylthio, hydroxyalkyl, haloalkyl, haloalkyloxy, aryl, heteroaryl, or R$^{19}$ is absent and R$^3$ is S forming a double bond with the carbon atom of the ring system to which it is attached;

R$^8$ is independently H, COR$^2$, CO$_2$R$^2$, SOR$^2$, SO$_2$R$^2$, SO$_3$R$^2$, alkyl, cycloalkyl, alkoxy, —NH$_2$, alkylamine, —NR$^{11}$COR$^2$, halogen, —OH, —SH, alkylthio, hydroxyalkyl, haloalkyl, haloalkyloxy, aryl or heteroaryl;

R$^{11}$ is independently H, alkyl, cycloalkyl, alkoxy, —OH, —SH, alkylthio, hydroxyalkyl, aryl, or heteroaryl;

R$^{19}$ is independently polycyclic aromatic ring system, heteroaryl or cycloalkyl;

R' is independently H, —CO$_2$R'', —CONHR'', —CR''O, —SO$_2$NR'', —NH$_2$, —NR$^{11}$COR$^2$, —NO$_2$, —NR$^{11}$—SO$_2$-haloalkyl, —NR$^{11}$—SO$_2$-alkyl, —SO$_2$-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R'' is independently H, —NH$_2$, haloalkyl, hydroxyalkyl, alkyl, cycloalkyl, aryl, heteroaryl or aminoalkyl;

R'" is independently —CO$_2$R", —CONHR", —CR"O, —SO$_2$NR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

The present invention relates to compounds of the general formula (III) or a salt or a physiologically functional derivative or a stereoisomer thereof,

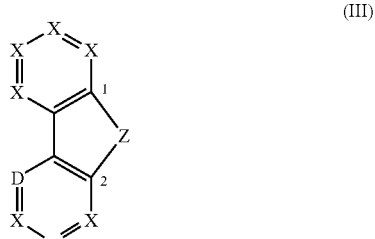

(III)

wherein
D is C—R$^{8'}$ or N;
X is C—R$^8$ or N;
Z is independently one of the following groups:

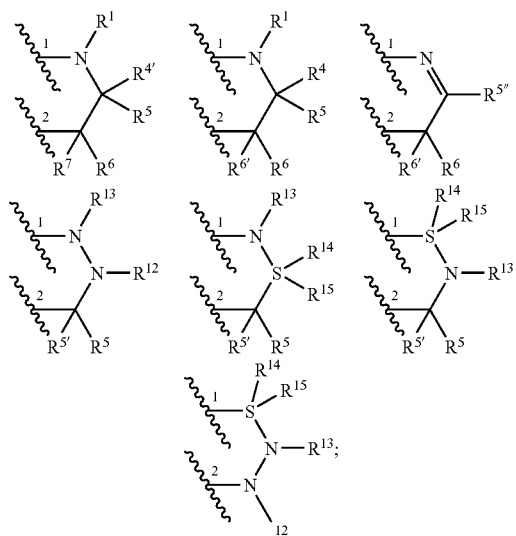

with the proviso that if Z is independently one of the following groups:

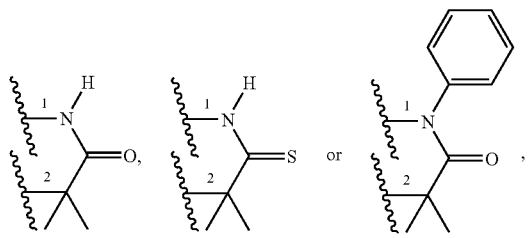

then D is C—R$^{8'}$;
R$^1$ is independently H, COR$^2$, CO$_2$R$^2$, SOR$^2$, SO$_2$R$^2$, SO$_3$R$^2$, alkyl, cycloalkyl, alkoxy, —OH, —SH, alkylthio, hydroxyalkyl, haloalkyl, haloalkyloxy, aryl or heteroaryl;

R$^2$ is independently H, alkyl, cycloalkyl, —NH$_2$, alkylamine, aryl or heteroaryl;

R$^4$ is independently COR$^2$, CO$_2$R$^2$, SOR$^2$, SO$_2$R$^2$, SO$_3$R$^2$, alkyl, cycloalkyl, alkoxy, alkylamine, —OH, —SH, alkylthio, hydroxyalkyl, haloalkyl, haloalkyloxy, aryl, heteroaryl;

R$^{4'}$ is independently H, COR$^2$, CO$_2$R$^2$, SOR$^2$, SO$_2$R$^2$, SO$_3$R$^2$, alkyl, cycloalkyl, alkoxy, alkylamine, —OH, —SH, alkylthio, hydroxyalkyl, haloalkyl, haloalkyloxy, aryl, heteroaryl;

R$^5$ is independently H, COR$^2$, CO$_2$R$^2$, SOR$^2$, SO$_2$R$^2$, SO$_3$R$^2$, alkyl, cycloalkyl, alkoxy, —NH$_2$, alkylamine, —NR$^{11}$COR$^2$, —OH, —SH, alkylthio, hydroxyalkyl, haloalkyl, haloalkyloxy, aryl, heteroaryl;

or R$^4$ is absent and R$^5$ is O or S forming a double bond with the carbon atom of the ring system to which it is attached;

or R$^{4'}$ is absent and R$^5$ is O or S forming a double bond with the carbon atom of the ring system to which it is attached;

R$^{5'}$ is independently H, COR$^2$, CO$_2$R$^2$, SOR$^2$, SO$_2$R$^2$, SO$_3$R$^2$, alkyl, cycloalkyl, alkoxy, alkylamine, —OH, —SH, alkylthio, hydroxyalkyl, haloalkyl, haloalkyloxy, aryl, heteroaryl;

or R$^5$ is absent and R$^{5'}$ is O or S forming a double bond with the carbon atom of the ring system to which it is attached;

R$^{5''}$ is independently H, COR$^2$, CO$_2$R$^2$, SOR$^2$, SO$_2$R$^2$, SO$_3$R$^2$, alkyl, cycloalkyl, alkoxy, —NH$_2$, alkylamine, —NR$^{11}$COR$^2$, —OH, —SH, alkylthio, hydroxyalkyl, haloalkyl, haloalkyloxy, aryl, or heteroaryl;

R$^6$ is independently H, COR$^2$, CO$_2$R$^2$, SOR$^2$, SO$_2$R$^2$, SO$_3$R$^2$, alkyl, cycloalkyl, alkoxy, —OH, —SH, alkylthio, hydroxyalkyl, haloalkyl, haloalkyloxy, aryl, heteroaryl;

R$^{6'}$ is independently H, COR$^2$, CO$_2$R$^2$, SOR$^2$, SO$_2$R$^2$, SO$_3$R$^2$, alkyl, cycloalkyl, alkoxy, —OH, —SH, alkylthio, hydroxyalkyl, haloalkyl, haloalkyloxy, aryl, heteroaryl;

or R$^6$ is absent and R$^{6'}$ is O or S forming a double bond with the carbon atom of the ring system to which it is attached;

R$^7$ is independently COR$^2$, CO$_2$R$^2$, SOR$^2$, SO$_2$R$^2$, SO$_3$R$^2$, alkyl, cycloalkyl, alkoxy, —OH, —SH, alkylthio, hydroxyalkyl, haloalkyl, haloalkyloxy, aryl, heteroaryl;

or R$^6$ is absent and R$^7$ is O or S forming a double bond with the carbon atom of the ring system to which it is attached;

R$^8$ is independently H, COR$^2$, CO$_2$R$^2$, SOR$^2$, SO$_2$R$^2$, SO$_3$R$^2$, alkyl, cycloalkyl, alkoxy, —NH$_2$, alkylamine, —NR$^{11}$COR$^2$, halogen, —OH, —SH, alkylthio, hydroxyalkyl, haloalkyl, haloalkyloxy, aryl or heteroaryl;

R$^{8'}$ is independently H, COR$^2$, CO$_2$R$^2$, SOR$^2$, SO$_2$R$^2$, SO$_3$R$^2$, alkyl, cycloalkyl, alkoxy, —NH$_2$, alkylamine, —NR$^{11}$COR$^2$, halogen, —OH, —SH, alkylthio, hydroxyalkyl, haloalkyl, haloalkyloxy, aryl or heteroaryl;

R$^{11}$ is independently H, alkyl, cycloalkyl, alkoxy, —OH, —SH, alkylthio, hydroxyalkyl, aryl, or heteroaryl;

R$^{12}$ is independently H, alkyl, cycloalkyl, alkoxy, —OH, —SH, alkylthio, hydroxyalkyl, aryl, heteroaryl, COR$^2$, SOR$^2$, SO$_2$R$^2$, SO$_3$R$^2$;

R$^{13}$ is independently H, alkyl, cycloalkyl, alkoxy, —OH, —SH, alkylthio, hydroxyalkyl, aryl, heteroaryl, COR$^2$, SOR$^2$, SO$_2$R$^2$, SO$_3$R$^2$;

R$^{14}$ is independently H, alkyl, cycloalkyl, alkoxy, —OH, hydroxyalkyl, aryl, heteroaryl, or R$^{15}$ is absent and R$^{14}$ is O or two O each forming a double bond with the sulfur atom of the ring system to which it is attached;

$R^{15}$ is independently H, alkyl, cycloalkyl, alkoxy, —OH, hydroxyalkyl, aryl, heteroaryl;

for the use as a medicament.

The present invention relates to compounds of the general formula (IV) or a salt or a physiologically functional derivative or a stereoisomer thereof,

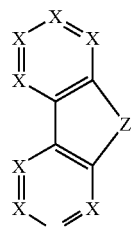

(IV)

wherein
X is C—$R^8$ or N;
Z is independently one of the following groups:

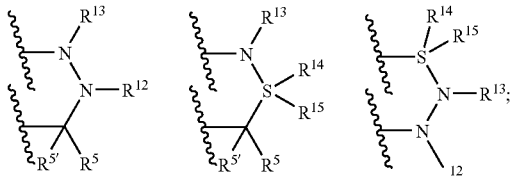

$R^5$ is independently H, $COR^2$, $CO_2R^2$, $SOR^2$, $SO_2R^2$, $SO_3R^2$, alkyl, cycloalkyl, alkoxy, —$NH_2$, alkylamine, —$NR^{11}COR^2$, —OH, —SH, alkylthio, hydroxyalkyl, haloalkyl, haloalkyloxy, aryl, heteroaryl;

$R_{5'}$ is independently H, $COR^2$, $CO_2R^2$, $SOR^2$, $SO_2R^2$, $SO_3R^2$, alkyl, cycloalkyl, alkoxy, alkylamine, —OH, —SH, alkylthio, hydroxyalkyl, haloalkyl, haloalkyloxy, aryl, heteroaryl;
  or $R^5$ is absent and $R^{5'}$ is O or S forming a double bond with the carbon atom of the ring system to which it is attached;

$R^8$ is independently H, $COR^2$, $CO_2R^2$, $SOR^2$, $SO_2R^2$, $SO_3R^2$, alkyl, cycloalkyl, alkoxy, —$NH_2$, alkylamine, —$NR^{11}COR^2$, halogen, —OH, —SH, alkylthio, hydroxyalkyl, haloalkyl, haloalkyloxy, aryl or heteroaryl;

$R^{12}$ is independently H, alkyl, cycloalkyl, alkoxy, —OH, —SH, alkylthio, hydroxyalkyl, aryl, heteroaryl, $COR^2$, $SOR^2$, $SO_2R^2$, $SO_3R^2$;

$R^{13}$ is independently H, alkyl, cycloalkyl, alkoxy, —OH, —SH, alkylthio, hydroxyalkyl, aryl, heteroaryl, $COR^2$, $SOR^2$, $SO_2R^2$, $SO_3R^2$;

$R^{14}$ is independently H, alkyl, cycloalkyl, alkoxy, —OH, hydroxyalkyl, aryl, heteroaryl, or $R^{15}$ is absent and $R^{14}$ is O or two O each forming a double bond with the sulfur atom of the ring system to which it is attached;

$R^{15}$ is independently H, alkyl, cycloalkyl, alkoxy, —OH, hydroxyalkyl, aryl, heteroaryl;

an $C_2$-$C_6$-alkyl group denotes a linear or branched $C_2$-$C_6$-alkyl, preferably a linear or branched chain of one to five carbon atoms, a linear or branched $C_2$-$C_6$-alkenyl or a linear or branched $C_2$-$C_6$-alkinyl group, which can optionally be substituted by one or more substituents R';

an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkinyl group, which can optionally be substituted by one or more substituents R';

the $C_1$-$C_6$-alkyl, $C_2$-$C_6$-alkenyl and $C_2$-$C_6$-alkinyl residue may be selected from the group comprising —$CH_3$, —$C_2H_5$, —CH═$CH_2$, —C≡CH, —$C_3H_7$, —CH($CH_3$)$_2$, —$CH_2$—CH═$CH_2$, —C($CH_3$)═$CH_2$, —CH═CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C(R')$_3$, —$C_2$(R')$_5$, —$CH_2$—C(R')$_3$, —$C_3$(R')$_7$, —$C_2H_4$—C(R')$_3$, —$C_2H_4$—CH═$CH_2$, —CH═CH—$C_2H_5$, —CH═C($CH_3$)$_2$, —$CH_2$—CH═CH—$CH_3$, —CH═CH—CH═$CH_2$, —$C_2H_4$—C≡CH, —C≡C—$C_2H_5$, —$CH_2$—C≡C—$CH_3$, —C≡C—CH═$CH_2$, —CH═CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH═$CH_2$, —CH═CH—$C_3H_7$, —$C_2H_4$—CH═CH—$CH_3$, —$CH_2$CH═CH—$C_2H_5$, —$CH_2$—CH═CH—CH═$CH_2$, —CH═CH—CH═CH—$CH_3$, —CH═CH—$CH_2$—CH═$CH_2$, —C($CH_3$)═CH—CH═$CH_2$, —CH═C($CH_3$)—CH═$CH_2$, —CH═CH—C($CH_3$)═$CH_2$, —$CH_2$—CH═C($CH_3$)$_2$, C($CH_3$)═C($CH_3$)$_2$, —$C_3H_6$—C≡CH, —C≡C—$C_3H_7$, —$C_2H_4$—C≡C—$CH_3$, —$CH_2$—C≡C—$C_2C_5$, —$CH_2$—C≡C—CH═$CH_2$, —$CH_2$—CH═CH—C≡CH, —$CH_2$—C≡C—C≡CH, —C≡C—CH═CH—$CH_3$, —CH═CH—C≡C—$CH_3$, —C≡C—C≡C—$CH_3$, —C≡C—$CH_2$—CH═$CH_2$, —CH═CH—$CH_2$—C≡CH, —C≡C—$CH_2$—C≡CH, —C($CH_3$)═CH—CH═$CH_2$, —CH═C($CH_3$)—CH═$CH_2$, —CH═CH—C($CH_3$)═$CH_2$, —C($CH_3$)═CH—C≡CH, —CH═C($CH_3$)—C≡CH, —CH═C($CH_3$)—C≡CH, —C≡C—C($CH_3$)═$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH═$CH_2$, —CH═CH—$C_4H_9$, —$C_3H_6$—CH═CH—$CH_3$, —$CH_2$—CH═CH—$C_3H_7$, —$C_2H_4$—C═CH—$C_2H_5$, —$CH_2$—C($CH_3$)═C($CH_3$)$_2$, —$C_2H_4$—CH═C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;

R' is independently H, —$CO_2R"$, —CONHR", —CR"O, —$SO_2NR"$, —NR"—CO-haloalkyl, —$NO_2$, —NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" is independently H, haloalkyl, hydroxyalkyl, alkyl, cycloalkyl, aryl, heteroaryl or aminoalkyl;

a cycloalkyl group denotes a non-aromatic ring system containing three to eight carbon atoms, preferably four to eight carbon atoms, wherein one or more of the carbon atoms in the ring can be substituted by a group E, E being O, S, SO, $SO_2$, N, or NR", R" being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C($R^{10}$)$_3$, —C$R^{10}$($R^{10'}$)$_2$, —C$R^{10}$($R^{10'}$)$R^{10''}$, —C$_2$($R^{10}$)$_5$, —CH$_2$—C($R^{10}$)$_3$, —CH$_2$—C$R^{10}$($R^{10'}$)$_2$, —CH$_2$—C$R^{10}$($R^{10'}$)$R^{10''}$, —C$_3$($R^{10}$)$_7$, or —C$_2$H$_4$—C($R^{10}$)$_3$, wherein $R^{10'}$, $R^{10'}$, $R^{10''}$, represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)$_3$, —OC$R^{10}$($R^{10'}$)$_2$, —OC$R^{10}$($R^{10'}$)$R^{10''}$, —OC$_2$($R^{10}$)$_5$, —OCH$_2$—C($R^{10}$)$_3$, —OCH$_2$—C$R^{10}$($R^{10'}$)$_2$, —OCH$_2$—C$R^{10}$($R^{10'}$)$R^{10''}$, —OC$_3$($R^{10}$)$_7$ or —OC$_2$H$_4$—C($R^{10}$)$_3$, wherein $R^{10}$, $R^{10'}$, $R^{10''}$ represent F, Cl, Br or I, preferably F;

a hydroxyalkylamino group denotes an (HO-alkyl)$_2$—N— group or HO-alkyl-NH— group, the alkyl group being as defined above;

an alkylamino group denotes an HN-alkyl or N-dialkyl group, the alkyl group being as defined above;

a halogen group is chlorine, bromine, fluorine or iodine;

a polycyclic aromatic ring system denotes an aromatic ring system in which two or more aryl groups and/or heteroaryl groups are fused, which can optionally be substituted by one or more substituents R', where R' is as defined above; the polycyclic aromatic ring system is preferably 1-naphthyl, 2-naphthyl, 1-anthracenyl or 2-anthracenyl;

an aryl group denotes an aromatic group having five to fifteen carbon atoms, which can optionally be substituted by one or more substituents R', where R' is as defined above; the aryl group is preferably a phenyl group, -o-C$_6$H$_4$—R', -m-C$_6$H$_4$—R', -p-C$_6$H$_4$—R", 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, 2-indolyl, 3-indolyl, 2-indolinyl, 3-indolinyl, benzo[b]furanyl, benzo[b]thiophenyl, benzimidazolyl, benzothiazolyl, quinazolinyl, quinoxalinyl, quinolinyl, tetrahydroquinolinyl, isoquinolinyl, or tetrahydroisoquinolinyl group. This heterocyclic group can optionally be substituted by one or more substituents R', wherein R' is as defined above.

The invention also provides a pharmaceutical composition comprising a compound of formula (I), formula (II), formula (III), or formula (IV) in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

In addition, the present invention provides methods for preparing the compounds of the invention such as compounds of formula (I), formula (II), formula (III), or formula (IV).

The compounds of formula (I) may be obtained via various methods. One possibility for the synthesis of compounds of formula (I), wherein $R^1$ and $R^4$ are as defined above and $R^3$ is hydrogen, comprises the step of reacting a compound of formula (V), wherein $R^4$ is as defined above, with a condensing agent like e.g. phosphorous oxychloride, phosphorous pentoxide, polyphosphoric acid, or zinc(II)-chloride (Bischler-Napieralski reaction, also called Pictet-Hubert reaction, or Morgan-Walls reaction), subsequent reduction using for example Sn/HCl, lithium aluminium hydride, sodium borohydride, hydrogen/platinum, hydrogen/platinum(IV)-oxide, raney-nickel, and other, and finally reaction of the resulting dihydrophenanthridine derivative using an electrophile $R^1$—LG, wherein $R^1$ is as defined above and LG (leaving group) comprising a leaving group like I, Br, Cl, tosyl, triflyl, or mesyl. Such a process is for example described in A. K. Sheinkman, A. P. Kucherenko, S. N. Baranov, Chem. HeterocycL. Compd. 1972, 8, 607-610 (Khim. Get. Soedin. 1972, 669-672). The reduction step may be performed in an enantioselective manner to obtain a compound of formula (I) wherein one enantiomer is enriched.

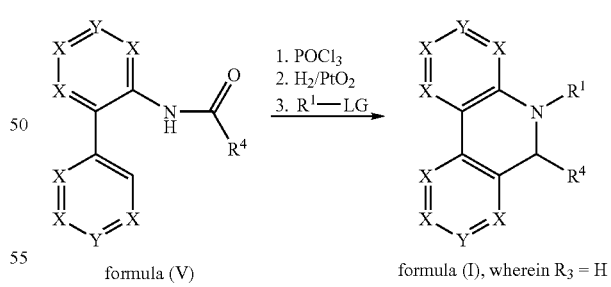

formula (V)   formula (I), wherein $R_3$ = H

One possibility for the synthesis of compounds of formula (I), wherein X=C—$R^8$, Y=C—$R^9$, $R^3$=H, and $R^8$ is as defined above, comprises the step of reacting a compound of formula (VI), wherein $R^8$ and $R^9$ are as defined above, with an organometallic compound $R^4$—M, wherein $R^4$ is as defined above and M comprising a group like —Li, —MgI, —MgBr, —MgCl, —ZnI, —ZnBr, —ZnCl, or —B(alkyl)$_2$, and subsequent reaction with an electrophile $R^1$—LG, wherein $R^1$ and LG is as defined above.

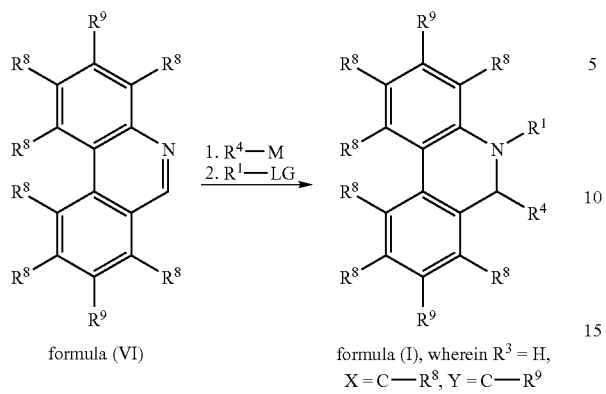

formula (VI)  →  formula (I), wherein $R^3$ = H, $X = C—R^8$, $Y = C—R^9$

1. $R^4$—M
2. $R^1$—LG

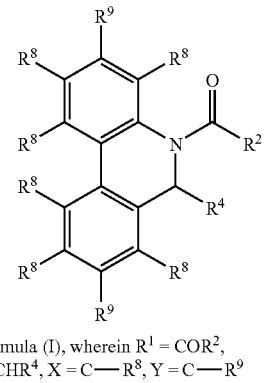

formula (I), wherein $R^1 = COR^2$, $A = CHR^4$, $X = C—R^8$, $Y = C—R^9$

One possibility for the synthesis of compounds of formula (I), wherein $R^1$=$COR^2$ or $CO_2R^2$ or $(CO)_2OR^2$, A=$CHR^4$, X=C—$R^8$, Y=C—$R^9$ and $R^2$, $R^4$, $R^8$ and $R^9$ are as defined above, comprises the step of reacting a compound of formula (VI), wherein $R^8$ and $R^9$ are as defined above, with an acid chloride $R^2COCl$ or a chloroformate $R^2OCOCl$ or an oxalic acid ester chloride $R^2O(CO)_2Cl$, respectively, wherein $R^2$ is as defined above, and a nucleophile $R^4$—H or $R^4$—M, wherein $R^4$ and M are as defined above. Preferably, $R^4$—H is an optionally substituted or unsubstituted indole or pyrrole or a silyl enol ether. A Lewis acid like for example $SbCl_5$, $TiCl_4$, $BF_3\times OEt_2$, TMSOTf, $InCl_3$ or other may be added. Such reactions are for example described in H. E. Zaugg, *Synthesis* 1984, 85-110; A. K. Sheinkman, A. P. Kucherenko, S. N. Baranov, *Chem. Heterocycl. Compd.* 1972, 8, 607-610 (*Khim. Get. Soedin.* 1972, 669-672); A. K. Sheinkman, E. N. Nelin, V. P. Marshtupa, V. I. Rybachenko, *Chem. Heterocycl. Compd* 1976, 12, 414-416 (*Khim. Get. Soedin.* 1976, 493-496); A. N. Kost, S. I. Suminov, "N-Acylpyridinium Salts", in *Adv. Org. Chem.* (Eds., H. Böhme, H. G. Viehe), Part 2, Wiley, 1979, 573-654. Enantiomerically enriched compounds of formula (I) may be obtained by using an enantiomerically enriched acid chloride $R^2COCl$ or chloroformate $R^2OCOCl$, respectively, as an auxiliary group that may subsequently be replaced by a group $R^1$.

Another possibility for the synthesis of compounds of formula (I), wherein $R^3$=H, and $R^1$, $R^4$, X and Y are as defined above, comprises the step of oxidising a compound of formula (VII), and $R^1$, X and Y are as defined above, to the corresponding N-acylphenanthridinium salt by using for example trityl tetrafluoroborate or another oxidizing agent, and subsequent reaction of this salt with a nucleophile $R^4$—H or $R^4$—M, wherein $R^4$ and M are as defined above, in the presence or in absence of a Lewis acid like for example $SbCl_5$, $TiCl_4$, $BF_3\times OEt_2$, TMSOTf, $InCl_3$ or other. Such a process is for example described in M. Ludwig, K. Polbom, K. T. Wanner, *Heterocycles* 2003, 61, 299-326. Enantiomerically enriched compounds of formula (I) may be obtained by using an enantiomerically enriched group $R^1$ as an auxiliary group that may be subsequently replaced by another group $R^1$.

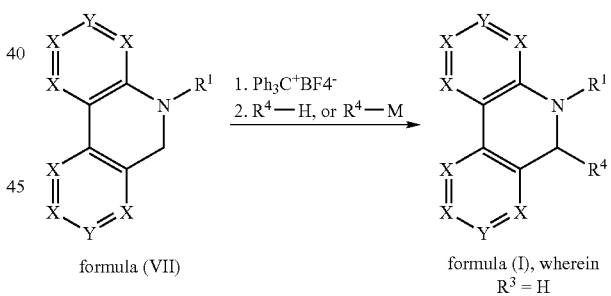

formula (VII)  →  formula (I), wherein $R^3$ = H

1. $Ph_3C^+BF_4^-$
2. $R^4$—H, or $R^4$—M

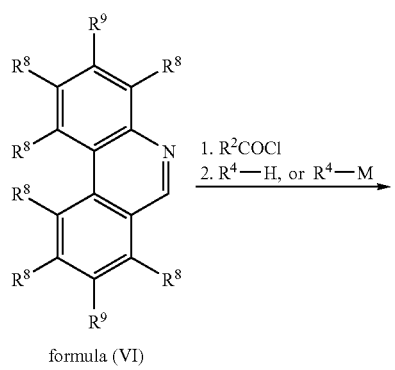

formula (VI)

1. $R^2COCl$
2. $R^4$—H, or $R^4$—M

The compounds of formula (II) may be obtained via various methods. One possibility for the synthesis of compounds of formula (II), wherein $R^1$ and $R^{19}$ are as defined above and $R^3$=H comprises the step of reacting a compound of formula (VIII), wherein $R^{19}$ and X are as defined above, with a condensing agent like e.g. phosphorous oxychloride, phosphorous pentoxide, polyphosphoric acid, or zinc(II)-chloride (Bischler-Napieralski reaction, also called Pictet-Hubert reaction, or Morgan-Walls reaction), subsequent reduction using for example Sn/HCl, lithium aluminium hydride, sodium borohydride, hydrogen/platinum, hydrogen/platinum(IV)-oxide, raney-nickel, and other, and finally reaction of the resulting dihydrophenanthridine derivative using an electrophile $R^1$—LG, wherein $R^1$ and LG are as defined above. Such a process is for example described in A.

K. Sheimman, A. P. Kucherenko, S. N. Baranov, *Chem. Heterocycl. Compd.* 1972, 8, 607-610 (*Khim. Get. Soedin.* 1972, 669-672). The reduction step may be performed in an enantioselective manner to obtain a compound of formula (I) wherein one enantiomer is enriched.

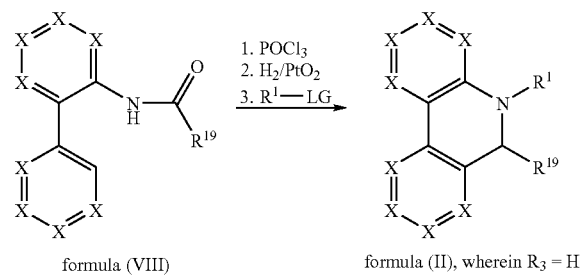

formula (VIII) → formula (II), wherein $R_3$ = H

One possibility for the synthesis of compounds of formula (II), wherein X=C—$R^8$, $R^3$=H, and $R^8$ and $R^{19}$ are as defined above, comprises the step of reacting a compound of formula (IX), wherein $R^8$ is as defined above, with an organometallic compound $R^{19}$—M, wherein $R^{19}$ and M are as defined above, and subsequent reaction with an electrophile $R^1$—LG, wherein $R^1$ and LG are as defined above.

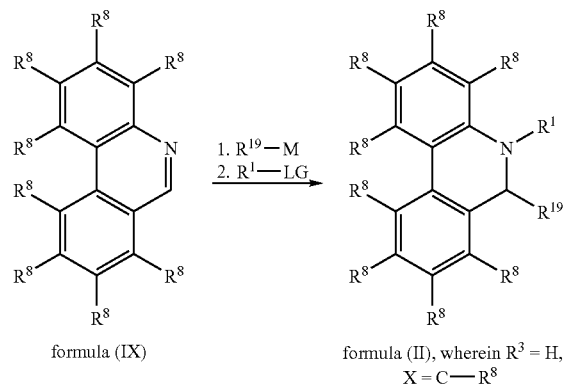

formula (IX) → formula (II), wherein $R^3$ = H, X = C—$R^8$

One possibility for the synthesis of compounds of formula (II), wherein $R^1$=COR$^2$ or CO$_2$R$^2$ or (CO)$_2$OR$^2$, $R^3$=H, X=C—$R^8$, and $R^2$, $R^8$ and $R^{19}$ are as defined above, comprises the step of reacting a compound of formula (IX), wherein $R^8$ is as defined above, with an a acid chloride R$^2$COCl or a chloroformate R$^2$OCOCl or an oxalic acid ester chloride R$^2$O(CO)$_2$Cl, respectively, and a nucleophile $R^{19}$—H or $R^{19}$—M, wherein $R^{19}$ and M are as defined above. Preferably, $R^{19}$—H is an optionally substituted or unsubstituted indole or pyrrole. A Lewis acid like for example SbCl$_5$, TiCl$_4$, BF$_3$×OEt$_2$, TMSOTf, InCl$_3$ or other may be added. Such reactions are for example described in H. E. Zaugg, *Synthesis* 1984, 85-110; A. K. Sheinkman, A. P. Kucherenko, S. N. Baranov, *Chem. Heterocycl. Compd.* 1972, 8, 607-610 (*Khim. Get. Soedin.* 1972, 669-672); A. K. Sheinkman, E. N. Nelin, V. P. Marshtupa, V. I. Rybachenko, *Chem. Heterocycl. Compd.* 1976, 12, 414-416 (*Khim. Get. Soedin.* 1976, 493-496); A. N. Kost, S. I. Suminov, "N-Acylpyridinium Salts", in *Adv. Org. Chem.* (Eds., H. Böhme, H. G. Viehe), Part 2, Wiley, 1979, 573-654. Enantiomerically enriched compounds of formula (II) may be obtained by using an enantiomerically enriched acid chloride R$^2$COCl or chloroformate R$^2$OCOCl, respectively, as an auxiliary group that may subsequently be replaced by a group $R^1$.

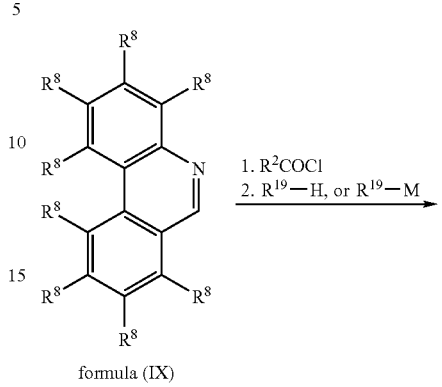

formula (IX)

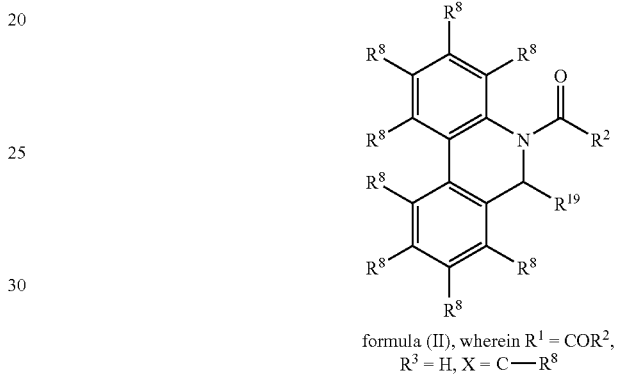

formula (II), wherein $R^1$ = COR$^2$, $R^3$ = H, X = C—$R^8$

Another possibility for the synthesis of compounds of formula (II), wherein $R^3$=H, and $R^1$ and X are as defined above, comprises the step of oxidising a compound of formula (X), wherein $R^1$ and X are as defined above, to the corresponding N-acylphenanthridinium salt by using for example trityl tetrafluoroborate or another oxidizing agent, and subsequent reaction of this salt with a nucleophile $R^{19}$—H or $R^{19}$—M, wherein $R^{19}$ is as defined above, and M comprises a residue like for example —Li, —MgI, —MgBr, —MgCl, —ZnI, —ZnBr, —ZnCl, —B(alkyl)$_2$ and other, in the presence or in absence of a Lewis acid like for example SbCl$_5$, TiCl$_4$, BF$_3$×OEt$_2$, TMSOTf, InCl$_3$ or other. Such a process is for example described in M. Ludwig, K. Polborn, K. T. Wanner, *Heterocycles* 2003, 61, 299-326. Enantiomerically enriched compounds of formula (II) may be obtained by using an enantiomerically enriched group $R^1$ as an auxiliary group that may subsequently be replaced by another group $R^1$.

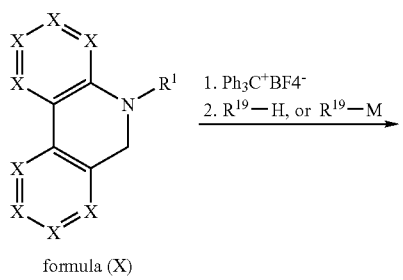

formula (X)

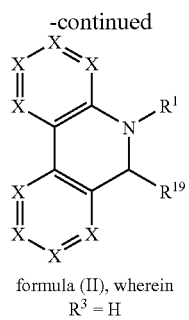

formula (II), wherein
R³ = H

The compounds of formula (III) may be obtained via various methods. One possibility for the synthesis of compounds of formula (III), wherein Z=—N(R¹³)—NH—C(=O)— and R¹³, D and X are as defined above, comprises the step of reacting a compound of formula (XI), wherein D and X are as defined above and R¹⁸ is for example OH, Cl, or alkoxy, with a compound of formula (XII), wherein X is as defined above, to obtain a compound of formula (XIII). The compound of formula (XIII) is reacted with an electrophile R¹³—LG, wherein R¹³ and LG are as defined above, and subsequently subjected to intramolecular cross coupling. Various types of cross coupling may be applied such as for example the Ullmann reaction (R¹⁶=R¹⁷=I), Suzuki cross coupling (R¹⁶=borono or dialkylborono or 4,4,5,5-tetramethyl-1,3,2-dioxaborolan-2-yl, and R¹⁷=I, Br, Cl, pseudohalogen; or R¹⁶=I, Br, Cl, pseudohalogen, and R¹⁷=borono or dialkylborono or 4,4,5,5-tetramethyl-1,3,2-dioxaborolan-2-yl), Stille cross coupling (R¹⁶=trialkylstannyl, and R¹⁷=I, Br, Cl, pseudohalogen; or R¹⁶=I, Br, Cl, pseudohalogen, and R¹⁷=trialkylstannyl) and other well known to those skilled in the art. The order of the steps may also be changed.

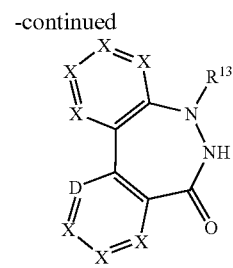

formula (III), Z = —N(R¹³)—NH—C(=O)—

One possibility for the synthesis of compounds of formula (III), wherein Z=—N(R¹³)—. C(R⁴)(H)—C(=O)— and R¹³, R⁴, D and X are as defined above, comprises the step of reacting a compound of formula (XIV), wherein R⁴, D and X and LG are as defined above, with a compound of formula (XV) to obtain a compound of formula (XVI), wherein R⁴, D and X are as defined above. The compound of formula (XVI) is reacted with an electrophile R¹³-LG, wherein R¹³ and LG are as defined above, and subsequently subjected to intramolecular cross coupling. Various types of cross coupling may be applied such as the Ullmann reaction (R¹⁶=R¹⁷=I), Suzuki cross coupling (R¹⁶=borono or dialkylborono or 4,4,5,5-tetramethyl-1,3,2-dioxaborolan-2-yl, and R¹⁷=I, Br, Cl, pseudohalogen; or R¹⁶=I, Br, Cl, pseudohalogen, and R¹⁷=borono or dialkylborono or 4,4,5,5-tetramethyl-1,3,2-dioxaborolan-2-yl), Stille cross coupling (R¹⁶=trialkylstannyl, and R¹⁷=I, Br, Cl, pseudohalogen; or R¹⁶=I, Br, Cl, pseudohalogen, and R¹⁷=trialkylstannyl) and others well known to those skilled in the art. The order of the steps may also be changed.

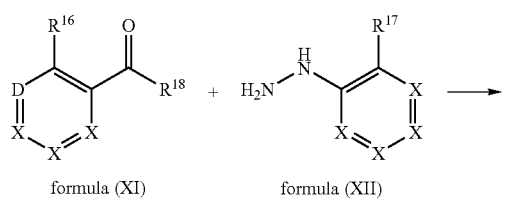

formula (XI)  formula (XII)

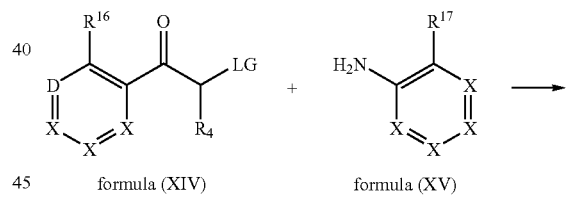

formula (XIV)  formula (XV)

formula (XIII)

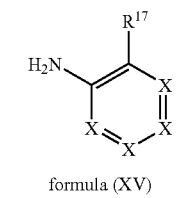

formula (XVI)

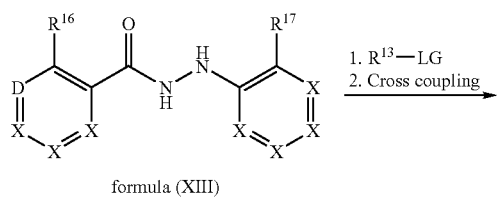

formula (XIII)

1. R¹³—LG
2. Cross coupling formula (XVI)

1. R¹³—LG
2. Cross coupling

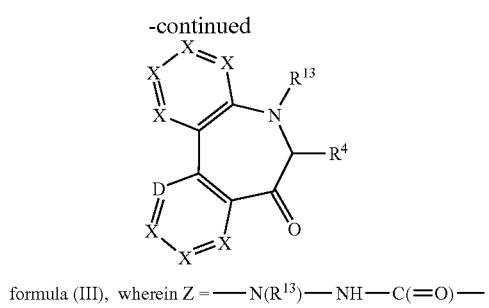

formula (III), wherein Z = —N(R$^{13}$)—NH—C(=O)—

One possibility for the synthesis of compounds of formula (III) wherein Z=—N=C(R$^{5''}$)—C(=O)— and D and X are as defined above comprises the step of treatment a compound of formula (III), wherein Z=—N(SO$_3$R$^2$)—CHR$^{5''}$—C(=O)— with a base like for example sodium methanolate or other. Such a process is for example described in W. Paterson, G. R. Proctor, *J. Chem. Soc.* 1962, 3468-3472; T. Eicher, A. Kruse, *Synthesis* 1985, 612-619.

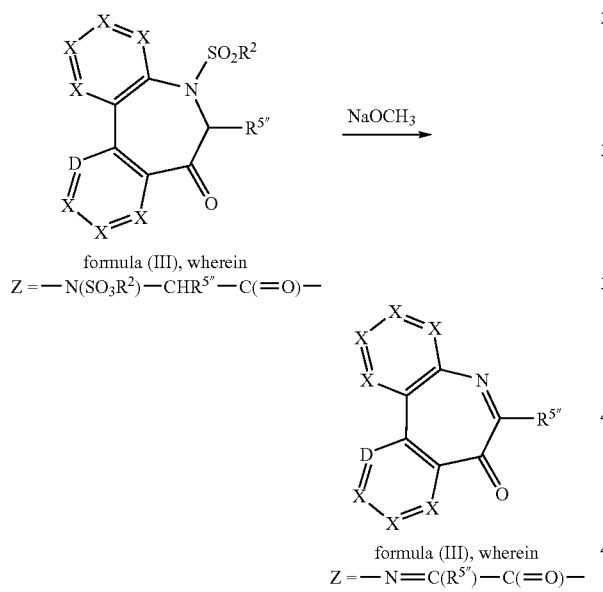

formula (III), wherein Z = —N(SO$_3$R$^2$)—CHR$^{5''}$—C(=O)—

NaOCH$_3$ → formula (III), wherein Z = —N=C(R$^{5''}$)—C(=O)—

The compounds of formula (IV) may be obtained via various methods. One possibility for the synthesis of compounds of formula (IV), wherein Z=—N(R$^{13}$)—NH—C(=O)— and R$^{13}$ and X are as defined above, comprises the step of reacting a compound of formula (XVII), wherein X is as defined above and R$^{18}$ is for example OH, Cl, or alkoxy, with a compound of formula (XVIII), wherein X is as defined above, to obtain a compound of formula (XIX). The compound of formula (XIX) is reacted with an electrophile R$^{13}$-LG, wherein R$^{13}$ and LG are as defined above, and subsequently subjected to intramolecular cross coupling. Various types of cross coupling may be applied such as for example the Ullmann reaction (R$^{16}$=R$^{17}$=I), Suzuki cross coupling (R$^{16}$=borono or dialkylborono or 4,4,5,5-tetramethyl-1,3,2-dioxaborolan-2-yl, and R$^{17}$=I, Br, Cl, pseudohalogen; or R$^{16}$=I, Br, Cl, pseudohalogen, and R$^{17}$=borono or dialkylborono or 4,4,5,5-tetramethyl-1,3,2-dioxaborolan-2-yl), Stille cross coupling (R$^{16}$=trialkylstannyl, and R$^{17}$=I, Br, Cl, pseudohalogen; or R$^{16}$=I, Br, Cl, pseudohalogen, and R$^{17}$=trialkylstannyl) and other well known to those skilled in the art. The order of the steps may also be changed.

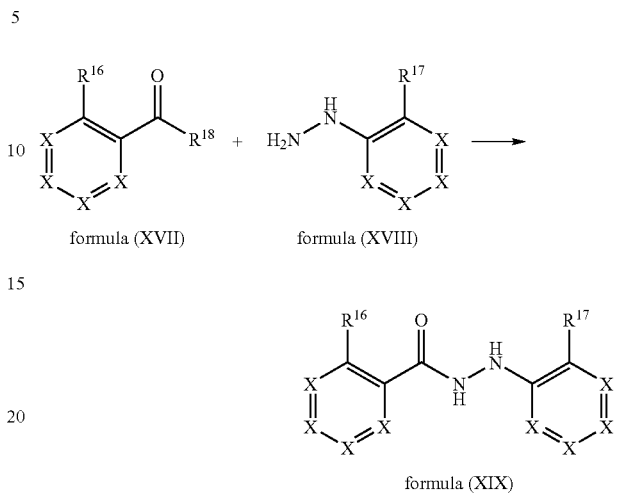

In a preferred embodiment of the invention, in the compounds of formula (I), R$^1$ is COR$^2$, CO$_2$R$^2$ or SO$_2$R$^2$ and R$^2$ is a alkyl, aryl or heteroaryl group, like optionally substituted phenyl.

In a preferred embodiment, in the compounds of formula (I), A=CR$^3$R$^4$.

In another preferred embodiment, in the compounds of formula (I), R$^3$ is H.

In another preferred embodiment, in the compounds of formula (I) R$^4$ is heteroaryl, more preferably 3-indolyl.

In another preferred embodiment, in the compounds of formula (I), X=CR$^8$ and R$^8$ is H.

In another preferred embodiment, in the compounds of formula (I) Y=CR$^9$ and R$^9$ is H.

In another preferred embodiment, in the compounds of formula (I), R$^{11}$ is H.

In particular preferred embodiment of the invention, in compounds of formula (I), X=CR$^8$ and R$^8$ is H and Y=CR$^9$ and R$^9$ is H and A=CR$^3$R$^4$ and R$^3$ is H, and R$^4$ is 3-indolyl.

In a more preferred embodiment of the invention, in compounds of formula (I), $X=CR^8$ and $R^8$ is H and $Y=CR^9$ and $R^9$ is H and $A=CR^3R^4$ and $R^3$ is H and $R^4$ is 3-indolyl and $R^1$ is $COR^2$ or $CO_2R^2$.

In a preferred embodiment of the invention, in the compounds of formula (II), $R^1$ is $COR^{2'}$, $CO_2R^2$ or $SO_2R^2$ and $R^{2'}$ is a $C_2$-$C_6$-alkyl, aryl or heteroaryl group, like substituted phenyl and $R^2$ is a alkyl, aryl or heteroaryl group, like optionally substituted phenyl.

In a preferred embodiment, in the compounds of formula (II), $R^3$ is H.

In another preferred embodiment, in the compounds of formula (II) $R^4$ is heteroaryl, more preferably 3-indolyl.

In another preferred embodiment, in the compounds of formula (II), $X=CR^8$ and $R^8$ is H.

In another preferred embodiment, in the compounds of formula (II), $R^{11}$ is H.

In particular preferred embodiment of the invention, in compounds of formula (II), $X=CR^8$ and $R^8$ is H and $A=CR^3R^4$ and $R^3$ is H, and $R^4$ is 3-indolyl.

In a more preferred embodiment of the invention, in compounds of formula (II), $X=CR^8$ and $R^8$ is H and $A=CR^3R^4$ and $R^3$ is H, and $R^4$ is 3-indolyl and $R^1$ is $COR^{2'}$ or $CO_2R^2$.

In a preferred embodiment of the invention, in the compounds of formula (III), $R^1$ is $COR^2$ or $SO_2R_2$ and $R^2$ is an alkyl, aryl or heteroaryl group, like optionally substituted phenyl.

In a preferred embodiment, in the compounds of formula (III), Z is one of the following groups:

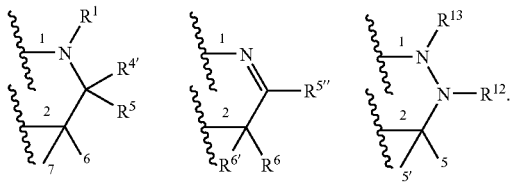

In another preferred embodiment, in the compounds of formula (III), $R^4$ and $R^5$ are H and $R^6$ is absent and $R^7$ is O forming a double bond with the carbon atom of the ring system to which it is attached.

In another preferred embodiment, in the compounds of formula (III) $R^{5''}$ is H, and $R^6$ is absent and $R^{6'}$ is O forming a double bond with the carbon atom of the ring system to which it is attached.

In another preferred embodiment, in the compounds of formula (III), $R^{13}$ is $COR^2$ or $SO_2R_2$ and $R^{12}$ is H and $R^5$ is absent and $R^{5'}$ is O forming a double bond with the carbon atom of the ring system to which it is attached.

In another preferred embodiment, in the compounds of formula (III), $R^{15}$ is absent and $R^{14}$ is O forming a double bond with the carbon atom of the ring system to which it is attached.

In another preferred embodiment, in the compounds of formula (III), $X=CR^8$ and $R^8$ is H.

In another preferred embodiment, in the compounds of formula (III) $D=CR^{8'}$ and $R^{8'}$ is H.

In another preferred embodiment, in the compounds of formula (III), $R^{11}$ is H.

In particular preferred embodiment of the invention, in compounds of formula (III), $X=CR^8$ and $R^8$ is H and $D=CR^{8'}$ and $R^{8'}$ is H and $R^1$ is $COR^2$ or $SO_2R^2$ and $R^2$ is an alkyl, aryl or heteroaryl group.

In a preferred embodiment, in the compounds of formula (IV), Z is the following group:

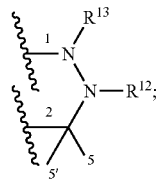

In another preferred embodiment, in the compounds of formula (IV), $R^{13}$ is $COR^2$ or $SO_2R^2$ and $R^{12}$ is H and $R^5$ is absent and $R^{5'}$ is O forming a double bond with the carbon atom of the ring system to which it is attached.

In another preferred embodiment, in the compounds of formula (IV), $R^{15}$ is absent and $R^{14}$ is two O each forming a double bond with the carbon atom of the ring system to which it is attached.

In another preferred embodiment, in the compounds of formula (IV), $X=CR^8$ and $R^8$ is H.

In another preferred embodiment, in the compounds of formula (IV), $R^{11}$ is H.

In particular preferred embodiment of the invention, in compounds of formula (IV) Z is the following group:

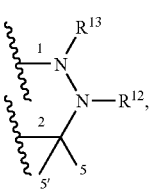

and $X=CR^8$ and $R^8$ is H and $R^5$ is absent and $R^{5'}$ is O forming a double bond with the carbon atom of the ring system to which it is attached and $R^{12}$ is H and $R^{13}$ is $COR^2$ or $CO_2R^2$ or $SO_2R^2$.

The compounds of the formula (I), formula (II), formula (III), or formula (IV), to be used according to the invention can form salts with inorganic or organic acids or bases. Examples of pharmaceutically acceptable salts comprise without limitation non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluene-sulfonic acid and others. Such salts can be produced by methods known to someone of skill in the art and described in the prior art.

Other salts like oxalate derived from oxalic acid, which is not considered as pharmaceutically acceptable can be appropriate as intermediates for the production of compounds of the formula (I), formula (II), formula (III), or formula (IV) or a pharmaceutically acceptable salt thereof or physiologically functional derivative or a stereoisomer thereof.

In one embodiment, the compounds of the formula (I), formula (II), formula (III), or formula (IV) may be used for treating and/or preventing diseases in which T cells play a role, especially inflammatory disorders and immune disorders such as Addison's disease, alopecia greata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harnman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granutomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Leishmania, and immunesuppressed disease states such as viral infections following allograft transplantations, AIDS, cancer, chronic active hepatitis diabetes, toxic chock syndrome and food poisoning.

Thus, in one embodiment, the invention relates to the use of the compounds of the formula (I), formula (II), formula (III), or formula (IV) or a pharmaceutically acceptable salt or physiologically functional derivative or a stereoisomer thereof if desired with appropriate adjuvants and additives for the production of a medicament for the treatment or prevention of a disease characterized by hyperproliferation of keratinocytes and/or T cells, especially inflammatory disorders and immune disorders, preferably selected from the group consisting of Addison's disease, alopecia greata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harnman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as *Leishmania*, and immunesuppressed disease states such as viral infections following allograft transplantations, AIDS, cancer, chronic active hepatitis diabetes, toxic chock syndrome and food poisoning.

Furthermore, the invention relates to a method of treatment or prevention of diseases which comprises the administration of an effective amount of compounds of the formula (I), formula (II), formula (III), or formula (IV) or a pharmaceutically acceptable salt or physiologically functional derivative or a stereoisomer thereof.

In a preferred embodiment the diseases for which the compounds of the present invention may be used are skin diseases in which T cells play a role. Preferred diseases are selected from the group consisting of psoriasis, atopic dermatitis, alopecia greata, alopecia totalis, alopecia subtotalis, alopecia universalis, alopecia diffusa, lupus erythematodes of the skin, lichen planus, dermatomyostis of the skin, atopic eczema, morphea, sklerodermia, psoriasis vulgaris, psoriasis capitis, psoriasis guttata, psoriasis inversa, alopecia greata ophiasis-type, androgenetic alopecia, allergic contact eczema, irritative contact eczema, contact eczema, pemphigus vulgaris, pemphigus foliaceus, pemphigus vegetans, scarring mucosal pemphigoid, bullous pemphgoid, mucous pemphigoid, dermatitis, dermatitis herpetiformis duhring, urticaria, necrobiosis lipoidica, erythema nodosum, lichen vidal, prurigo simplex, prurigo nodularis, prurigo acuta, linear IgA dermatosis, polymorphic light dermatoses, erythema solaris, lichen sclerosus et atrophicans, exanthema of the skin, drug exanthema, purpura chronica progressiva, dihidrotic eczema, Eczema, fixed drug exanthema, photoallergic skin reaction, lichen simplex eriorale, dermatitis and "Graft versus Host-Disease", acne, rosacea, scarring, keloids and vitiligo.

In a preferred embodiment, the invention relates to the use of compounds of the formula (I), formula (II), formula (III), or formula (IV) or a pharmaceutically acceptable salt or physiologically functional derivative or a stereoisomer thereof if desired with appropriate adjuvants and additives for the production of a medicament for the treatment or prevention of skin diseases in which T cells play a role; especially preferably the skin diseases are selected from the group consisting of psoriasis, atopic dermatitis, alopecia greata, alopecia totalis, alopecia subtotalis, alopecia universalis, alopecia diffusa, lupus erythematodes of the skin, lichen planus, dermatomyostis of the skin, atopic eczema, morphea, sklerodermia, psoriasis vulgaris, psoriasis capitis, psoriasis guttata, psoriasis inversa, alopecia greata ophiasis-type, androgenetic alopecia, allergic contact eczema, irritative contact eczema, contact eczema, pemphigus vulgaris, pemphigus foliaceus, pemphigus vegetans, scarring mucosal pemphigoid, bullous pemphgoid, mucous pemphigoid, dermatitis, dermatitis herpetiformis duhring, urticaria, necrobiosis lipoidica, erythema nodosum, lichen vidal, prurigo simplex, prurigo nodularis, prurigo acuta, linear IgA dermatosis, polymorphic light dermatoses, erythema solaris, lichen sclerosus et atrophicans, exanthema of the skin, drug exanthema, purpura chronica progressiva, dihidrotic eczema, Eczema, fixed drug exanthema, photoallergic skin reaction, lichen simplex eriorale, dermatitis and "Graft versus Host-Disease", acne, rosacea, scarring, keloids and vitiligo.

Especially preferred are skin diseases in which a hyperproliferation of keratinocytes plays a role. Especially preferred diseases are Psoriasis, atopic dermatitis, actinic keratoses, hyperkeratoses like epidermolytic hyperkeratosis, Hyperkeratosis Lenticularis Perstans, Keratosis pilaris and Ichthyoses.

In another preferred embodiment, the invention relates to the use of compounds of the formula (I), formula (II), formula (III), or formula (IV) or a pharmaceutically acceptable salt or physiologically functional derivative or a stereoisomer thereof if desired with appropriate adjuvants and additives for the production of a medicament for the treatment or prevention of skin diseases in which a hyperproliferation of keratinocytes plays a role, especially preferably the skin diseases are selected from the group consisting of psoriasis, atopic dermatitis, actinic keratoses, hyperkeratoses like epidermolytic hyperkeratosis, Hyperkeratosis Lenticularis Perstans, Keratosis pilaris and Ichthyoses.

"Treatment" according to the present invention is intended to mean complete or partial healing of a disease, or alleviation of a disease or stop of progression of a given disease.

Furthermore, the invention relates to a method of treatment or prevention of diseases which comprises the administration of an effective amount of compounds of the formula (I), formula (II), formula (III), or formula (IV) or a pharmaceutically acceptable salt or physiologically functional derivative or a stereoisomer thereof. In a preferred embodiment, the diseases are characterized by hyperproliferation of keratinocytes and/or T cells, especially inflammatory disorders and immune disorders, preferably selected from the group consisting of Addison's disease, alopecia greata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harnman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as *Leishmania*, and immunesuppressed disease states such as viral infections following allograft transplantations, AIDS, cancer, chronic active hepatitis diabetes, toxic chock syndrome and food poisoning. In a more preferred embodiment, the diseases are skin diseases in which T cells play a role, preferably the diseases are selected from the group consisting of psoriasis, atopic dermatitis, alopecia greata, alopecia totalis, alopecia subtotalis, alopecia universalis, alopecia diffusa, lupus erythematodes of the skin, lichen planus, dermatomyostis of the skin, atopic eczema, morphea, sklerodermia, psoriasis vulgaris, psoriasis capitis, psoriasis guttata, psoriasis inversa, alopecia greata ophiasis-type, androgenetic alopecia, allergic contact eczema, irritative contact eczema, contact eczema, pemphigus vulgaris, pemphigus foliaceus, pemphigus vegetans, scarring mucosal pemphigoid, bullous pemphgoid, mucous pemphigoid, dermatitis, dermatitis herpetiformis duhring, urticaria, necrobiosis lipoidica, erythema nodosum, lichen vidal, prurigo simplex, prurigo nodularis, prurigo acuta, linear IgA dermatosis, polymorphic light dermatoses, erythema solaris, lichen sclerosus et atrophicans, exanthema of the skin, drug exanthema, purpura chronica progressiva, dihidrotic eczema, Eczema, fixed drug exanthema, photoallergic skin reaction, lichen simplex eriorale, dermatitis and "Graft versus Host-Disease", acne, rosacea, scarring, keloids and vitiligo. In an even more preferred embodiment, the disease is a skin disease in which a hyperproliferation of keratinocytes plays a role. Especially preferred diseases are Psoriasis, atopic dermatitis, actinic keratoses, hyperkeratoses like epidermolytic hyperkeratosis, Hyperkeratosis Lenticularis Perstans, Keratosis pilaris and Ichthyoses.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention are also useful for the treatment of diseases which are caused by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, myeloma) or solid tumors (for example breast, prostate, liver, bladder, lung, esophageal, stomach, colorectal, genitourinary, gastrointestinal, skin, pancreatic, brain, uterine, colon, head and neck, and ovarian, melanoma, astrocytoma, small cell lung cancer, glioma, basal and squameous cell carcinoma, sarcomas as Kaposi's sarcoma and osteosarcoma).

The compounds of the present invention can further be used for diseases that are caused by protozoal infestations in humans and animals. Such veterinary and human pathogenic protozoas are preferably intracellular active parasites of the phylum Apicomplexa or Sarcomastigophora, especially *Trypanosoma*, Plasmodia, *Leishmania*, Babesia and Theileria, *Cryptosporidia*, Sacrocystida, Amoebia, *Coccidia* and *Trichomonadia*. These active substances or corresponding drugs are especially suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chargas disease, caused by *Trypanosoma cruzi*, sleeping sickness, caused by *Trypanosoma brucei rhodesiense* or *gambiense*, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Trypanosoma vivax vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing European bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, Eimeria and *Isospora* species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The compounds of the present invention can further be used for viral infections or other infections caused for instance by *Pneumocystis carinii*.

The compounds of formula (I), formula (II), formula (III), or formula (IV) and their pharmacologically acceptable salts can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one compound of the formula (I), formula (II), formula (III), or formula (IV) or a salt thereof, in addition to customary pharmaceutically innocuous excipients and additives. The compounds of formula (I), formula (II), formula (III), or formula (IV) can also be administered in form of their salts, which are obtainable by reacting the respective compounds with physiologically acceptable acids and bases.

The production of medicaments containing the compounds of formula (I), formula (II), formula (III), or formula (IV) according to the invention and their application can be performed according to well-known pharmaceutical methods.

While the compounds of formula (I), formula (II), formula (III), or formula (IV) according to the invention for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds may be anhydrous or solvated.

In a preferred embodiment, the invention provides medicaments comprising compounds of formula (I), formula (II), formula (III), or formula (IV) according to the invention, or a pharmaceutically acceptable salt or physiologically functional derivative or a stereoisomer thereof, together with one or more pharmaceutically acceptable carriers thereof, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such Medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound useable according to the invention can be administered in a wide variety of oral and parenteral dosage forms. It will be obvious to those skilled in the art that the following dosage forms may comprise, as the active component, either a compound of formula (I), formula (II), formula (III), or formula (IV) according to the invention or a pharmaceutically acceptable salt or stereosomer thereof.

For preparing a medicament from a compounds of formula (I), formula (II), formula (III), or formula (IV), pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it.

Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds of formula (I), formula (II), formula (III), or formula (IV) according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

In an especially preferred embodiment of the present invention the medicament is applied topically. This reduces possible side effects and limits the necessary treatment to those areas affected.

Preferably the medicament is prepared in form of an ointment, a gel, a plaster, an emulsion, a lotion, a foam, a cream of a mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

Pharmaceutical compositions can also contain two or more compounds of the formula (I), formula (II), formula (III), or formula (IV) or their pharmacologically acceptable salts and also other therapeutically active substances.

Thus, the compounds of the present invention can be used in the form of one compound alone or in combination with other active compounds—for example with medicaments already known for the treatment of the aforementioned diseases, whereby in the latter case a favorable additive, amplifying effect is noticed. Suitable amounts to be administered to humans range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

In general, a daily dose of approximately 10 mg to 5000 mg, preferably 50 to 500 mg, per human individual is appropriate in the case of the oral administration. In the case of other administration forms too, the daily dose is in similar ranges. For topical delivery, depending on the permeability of the skin, the type and the severity of the disease and dependent on the type of formulation and frequency of application, different concentrations of active compounds within the medicament can be sufficient to elicit a therapeutic effect by topical application. Preferably the concentration of an active compound or a pharmaceutically acceptable salt thereof or a physiologically functional derivative or a stereoisomer thereof within a medicament according to the invention is in the range of between 1 µmol/l and 100 mmol/l.

The following examples and figures are included to demonstrate preferred embodiments of the invention. It should be appreciated by those of skill in the art that the techniques disclosed in the examples that follow represent techniques discovered by the inventors to function well in the practice of the invention, and thus can be considered preferred modes for its practice. However, those of skill in the art should, in light of the present disclosure, appreciate that many changes can be made in the specific embodiments that are disclosed without departing from the spirit and scope of the invention as set out in the appended claims. All references cited are incorporated herein by reference.

EXAMPLES

Abbreviations: min, minute(s); h, hour(s); r.t., room temperature.

NMR spectra: Bruker Avance 300 MHz. The spectra were recorded at 300 MHz ($^1$H-NMR) and 75 MHz ($^{13}$C-NMR), respectively, using the residual solvent peak as an internal standard (DMSO-$d_6$, $\delta_H$=2.49 and $\delta_C$=39.70; CD$_3$OD, $\delta_H$=3.31; CDCl$_3$, $\delta_H$=7.26; CD$_3$CN, $\delta_H$=1.93).

Analytical LC/ESI-MS: 2×Waters 600 Multisolvent Delivery System. 50 µl sample loop. Column, Chromolith Speed ROD RP18e (Merck, Darmstadt), 50×4.6 mm, with 2 µm prefilter (Merck). Eluent A, H$_2$O+0.1% HCO$_2$H; eluent B, MeCN. Gradient, 5% B to 100% B within 5 min; flow, 3 ml/min. Waters LCZ single quadrupol mass spectrometer with electrospray source. MS method, MS8minPM-80-800-20V; positive/negative ion mode. scanning, m/z 80-800 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm.

Preparative HPLC-MS: Waters 600 Multisolvent Delivery System with preparative pump heads. 2000 µl or 5000 µl sample loop. Column, Waters X-Terra RP18, 7 µm, 19×150 mm with X-Terra RP18 guard cartridge 7 µm, 19×10 mm; used at flow rate 20 ml/min or YMC ODS-A, 120 Å, 40×150 mm with X-Terra RP18 guard cartridge 7 µm, 19×10 mm; used at flow rate 50 ml/min. Make-up solvent: MeCN—H$_2$O—HCO$_2$H 80:20:0.05 (v:v:v). Eluent A, H$_2$O+0.1% HCO$_2$H; eluent B, MeCN. Different linear gradients from 5-100% eluent B, adapted to sample. Injection volume: 500 µl -2000 µl depending on sample. Waters ZQ single quadrupol mass spectrometer with electrospray source. Positive or negative ion mode scanning m/z 80-800 in 1 s; capillary, 3.5 kV or 3.0 kV; cone voltage, 20 V; multiplier voltage, 400 V; probe and desolvation gas temperature, 120° C. and 350° C., respectively. Waters Fraction Collector II with mass-triggered fraction collection. Waters 996 photo diode array detector.

General Procedure 1 (GP 1): Synthesis of 5-acyl-5H-phenanthridine-6-ones. 5H-Phenanthridin-6-one (1.0 mmol) was dissolved in dry tetrahydrofuran (5 mL) in an argon atmosphere, and a few drops of dry dimethylformamide were added. Sodium hydride (1.1 mmol) was added in portions and the mixture was stirred for 20 min at r.t. A solution of the appropriate acid chloride (1.0 mmol) in dry tetrahydrofuran was added slowly and the mixture was allowed to stir for 1 h at r.t. The crude product was purified by silica gel chromatography using a petroleum ether/ethyl acetate gradient.

Example 1

5-Cyclobutanecarbonyl-5H-phenanthridin-6-one was prepared from 5H-phenanthridin-6-one and cyclobutanecarbonyl chloride according to GP 1. Yield, 2%. $^1$H-NMR (CD$_3$OD): δ=1.95-2.09 (m, 1H), 2.11-2.26 (m, 1H), 2.36-2.55 (m, 4H), 3.64 (ψ-quint, J=8.5 Hz, 1H), 7.32 ("t", J=7.5 Hz, 1H), 7.37 ("t", J=7.7 Hz, 1H), 7.47 ("t", J=7.5 Hz, 1H), 7.53 ("t", J=7.5 Hz, 1H), 7.70 (d, J=7.5 Hz, 1H), 7.74 (d, J=7.5 Hz, 1H), 7.90 (d, J=7.5 Hz, 1H), 8.22 (d, J=7.7 Hz, 1H); (+)-ESI-MS: m/z=278 [M+H]$^+$, 196 [5H-phenanthridin-6-one+H]$^+$.

Example 2

5-(Furan-2-carbonyl)-5H-phenanthridin-6-one was prepared from 5H-phenanthridin-6-one and 2-furoyl chloride according to GP 1. Yield, 2%. $^1$H-NMR (CD$_3$OD): δ=6.77 (dd, J=3.6 Hz, J=1.8 Hz, 1H), 7.44 (ddd, J=J=7.5 Hz, J=1.0 Hz, 1H), 7.41 (ddd, J=J=7.7 Hz, J=1.1 Hz, 1H), 7.48 (ddd, J=J=7.5 Hz, J=1.1 Hz, 1H), 7.54 (ddd, J=J=7.5 Hz, J=1.1 Hz, 1H), 7.57 (dd, J=3.6 Hz, J=0.7 Hz, 1H), 7.70 (d, J=7.5 Hz, 1H), 7.74 (d, J=7.5 Hz, 1H), 7.92 (d, J=7.5 Hz, 1H), 7.95 (dd, J=1.8 Hz, J=0.7 Hz, 1H), 8.47 (d, J=7.7 Hz, 1H); (+)-ESI-MS: m/z=290 [M+H]$^+$.

General Procedure 2 (GP 2): Synthesis of 6-Substituted 5-Acyl-5,6-dihydrophenanthridines.

Phenanthridine (1 mmol) was dissolved in dry toluene or dry tetrahydrofuran (2 to 5 mL) under an argon atmosphere. After cooling to 0° C., the appropriate acid chloride, or chloroformate, or oxalic acid ester chloride, respectively (1 mmol), was added dropwise.

The mixture was stirred for 2 h at r.t. and cooled to 0° C. again. Triethylamine (1 mmol) was added followed by the appropriate nucleophile (1 mmol). After stirring for 3 h at r.t., water was added and the mixture was extracted several times with ethyl acetate. After washing the combined organic phases with brine and drying over Na$_2$SO$_4$, the solvent was removed in vacuo. The product was purified by silica gel chromatography using a petroleum ether/ethyl acetate gradient.

Example 3

1-[6-(1H-Indol-3-yl)-6H-phenanthridin-5-yl]-ethanone was prepared from phenanthridine, acetyl chloride, and indole according to GP 2. Yield, 30%. $^1$H-NMR (CDCl$_3$): δ=2.25 (s, 3H), 6.16 (d, J=1.6 Hz, 1H), 7.10 (td, J=7.7 Hz, J=1.1 Hz, 1H), 7.12-7.17 (m, 2H), 7.18-7.25 (m, 2H), 7.31-7.48 (m, 3H), 7.50 (s, 1H), 7.73 (s, br., 1H), 7.81 (d, J=7.8 Hz, 1H), 7.89 (d, J=7.8 Hz, 1H), 7.93-8.00 (m, 1H); (+)-ESI-MS: m/z=339 [M+H]$^+$, 222 [M-indole+H]$^+$.

Example 4

[6-(1H-Indol-3-yl)-6H-phenanthridin-5-yl]-phenyl-methanone was prepared from phenanthridine, benzoyl chloride, and indole according to GP 2. Yield, 11%. $^1$H-NMR (DMSO-d$_6$): δ=6.20 (dd, J=2.5 Hz, J=0.8 Hz, 1H), 6.36 (s, br., 1H), 6,80 (t, J=7.6 Hz, 1H), 6.99-7.08 (m, 2H), 7.11 (ddd, J=J=7.5 Hz, J=1.2 Hz, 1H), 7.19-7.31 (m, 6H), 7.37 ("t", J=7.1 Hz, 1H), 7.43 ("t", J=7 Hz, 1H), 7.54 ("t", J=7 Hz, 2H), 7.85-7.90 (m, 1H), 7.95 (dd, J=7.8 Hz, J=1.2 Hz, 1H), 8.10 ("d", J=7.5 Hz, 1H), 10.69 (s, 1H); (+)-ESI-MS: m/z=401 [M+H]$^+$, 284 [M-indole+H]$^+$.

Example 5

[6-(1H-Indol-3-yl)-6H-phenanthridin-5-yl]-naphthalen-1-yl-methanone was prepared from phenanthridine, 1-naphthoyl chloride, and indole according to GP 2. Yield, 2%. (+)-ESI-MS: m/z=451 [M+H]$^+$, 334 [M-indole+H]$^+$.

Example 6

(4-Dimethylamino-phenyl)-[6-(1H-indol-3-yl)-6H-phenanthridin-5-yl]-methanone was prepared from phenanthridine, 4-dimethylaminobenzoyl chloride, and indole according to GP 2. Yield, 55%. (+)-ESI-MS: m/z=444 [M+H]$^+$, 327. [M-indole+H]$^+$, 148.

Example 7

[6-(1H-Indol-3-yl)-6H-phenanthridin-5-yl]-(4-trifluoromethyl-phenyl)-methanone was prepared from phenanthridine, 4-trifluoromethylbenzoyl chloride, and indole according to GP 2. Yield, 12%. $^1$H-NMR (CD$_3$OD): δ=6.19 (s, 1H), 6.28 (s, br., 1H), 6.75 (t, br., J≈6.8 Hz, 1H), 7.03-7.11 (m, 2H), 7.14 (t, J=7.6 Hz, 1H), 7.20-7.25 (m, 1H), 7.33-7.51 (m, 5H), 7.52-7.60 (m, 1H), 7.57 (d, J=7.6 Hz, 2H), 7.92 (d, J=7.8 Hz, 1H), 7.99 (s, br., 1H), 8.07 (d, J=7.8 Hz, 1H); (+)-ESI-MS: m/z=469 [M+H]$^+$, 352 [M-indole+H]$^+$.

Example 8

(4-tert-Butyl-phenyl)-[6-(1H-indol-3-yl)-6H-phenanthridin-5-yl]-methanone was prepared from phenanthridine, 4-tert-butylbenzoyl chloride, and indole according to GP 2. Yield, 34%. $^1$H-NMR (DMSO-d$_6$): δ=1.21 (s, 9 H), 6.20 (dd, J=2.5 Hz, J=0.8 Hz, 1H), 6.40 (d, br., J=7 Hz, 1H), 6.82 (t, J≈8 Hz, 1H), 6.99-7.08 (m, 2H), 7.11 (ddd, J=J=7.6 Hz, J=1.1 Hz, 1H), 7.14-7.19 (m, 3H), 7.22-7.27 (m, 1H), 7.30 ("d", J≈8.6 Hz, 2H), 7.43 (ddd, J≈J≈7.5 Hz, J=1.2 Hz, 1H), 7.50-7.57 (m, 2H), 7.85-7.90 (m, 1H), 7.95 (dd, J=7.8 Hz, J=1.3 Hz, 1H), 8.09 ("d", J=7.5 Hz, 1H), 10.69 (s, 1H); (+)-ESI-MS: m/z=457 [M+H]$^+$, 340 [M-indole+H]$^+$.

Example 9

[6-(1H-Indol-3-yl)-6H-phenanthridin-5-yl]-(4-methoxyphenyl)-methanone was prepared from phenanthridine, 4-methoxybenzoyl chloride, and indole according to GP 2. Yield, 67%. $^1$H-NMR (DMSO-d$_6$): δ=3.72 (s, 3H), 6.20 (dd, J=2.5 Hz, J=0.8 Hz, 1H), 6.39 (d, br., J=8 Hz, 1H), 6.81 (d, J=9.0 Hz, 2H), 6.81-6.88 (m, 1H), 6.98-7.08 (m, 2H), 7.12 (ddd, J=J=7.5 Hz, J=1.2 Hz, 1H), 7.15-7.26 (m, 2H), 7.18 (d, J=9.0 Hz, 2H), 7.42 (ddd, J=J=7.4 Hz, J=1.2 Hz, 1H), 7.53 ("t", J≈7 Hz, 2H), 7.90 ("d", J≈7 Hz, 1H), 7.95 (dd, J=7.9 Hz, J=1.3 Hz, 1H), 8.09 ("d", J≈8 Hz, 1H), 10.68 (s, 1H); (+)-ESI-MS: m/z=431 [M+H]$^+$, 314 [M-indole+H]$^+$.

Example 10

[6-(1H-Indol-3-yl)-6H-phenanthridin-5-yl]-m-tolyl-methanone was prepared from phenanthridine, m-toluoyl chloride, and indole according to GP 2. Yield, 13%. $^1$H-NMR (CD$_3$CN): δ=2.22 (s, 3H), 6.22 (dd, J=2.5 Hz, J=1.0 Hz, 1H), 6.41 (s, br., 1H), 6.75 (t, J=7.5 Hz, 1H), 6.96 (d, J=7.5 Hz, 1H), 7.06-7.15 (m, 4H), 7.15-7.21 (m, 2H), 7.24-7.31 (m, 2H), 7.43 (ddd, J=J=7.3 Hz, J=1.2 Hz, 1H), 7.47-7.59 (m, 2H), 7.88 (dd, J=7.8 Hz, J=1.0 Hz, 1H), 7.93-8.00 (m, 1H), 8.04 (d, J=7.7 Hz, 1H), 8.90 (s, br., 1H); (+)-ESI-MS: m/z=415 [M+H]$^+$, 298 [M-indole+H]$^+$.

Example 11

[6-(1H-Indol-3-yl)-6H-phenanthridin-5-yl]-(3-methoxyphenyl)-methanone was prepared from phenanthridine, 3-methoxybenzoyl chloride, and indole according to GP 2. Yield, 84%. $^1$H-NMR (CD$_3$OD): δ=3.62 (s, 3H), 6.19 (s, 1H), 6.37 (s, br., 1H), 6.71-6.86 (m, 3H), 6.91 (dd, J=8.1 Hz, J=1.9 Hz, 1H), 7.02-7.26 (m, 5H), 7.32 (s, br., 1H), 7.39-7.48 (m, 2H), 7.54 (td, J=7.1 Hz, J=2.5 Hz, 1H), 7.90 (dd, J=7.9 Hz, J=1.2 Hz, 1H), 7.97 (s, br., 1H), 8.06 (d, J=7.8 Hz, 1H); (+)-ESI-MS: m/z=431 [M+H]$^+$, 314 [M-indole+H]$^+$.

Example 12

(3-Fluoro-phenyl)-[6-(1H-indol-3-yl)-6H-phenanthridin-5-yl]-methanone was prepared from phenanthridine, 3-fluorobenzoyl chloride, and indole according to GP 2. Yield, 41%. $^1$H-NMR (DMSO-d$_6$): δ=6.21 (d, J=1.9 Hz, 1H), 6.41 (s, br., 1H), 6.84 (t, J=7.5 Hz, 1H), 6.96 (d, J=7.5 Hz, 1H), 6.99-7.11 (m, 3H), 7.14 (ddd, J=J=7.7 Hz, J=0.8 Hz, 1H), 7.17-7.35 (m, 4H), 7.43 (ddd, J=J=7.4 Hz, J=1.1 Hz, 1H), 7.54 ("t", J=7.2 Hz, 2H), 7.85 ("d", J=7 Hz, 1H), 7.97 (dd, J=7.9 Hz, J=1.2 Hz, 1H), 8.11 (d, J=7.5 Hz, 1H), 10.71 (s, br., 1H); (+)-ESI-MS: m/z=419 [M+H]$^+$, 302 [M−indole+H]$^+$.

Example 13

(3-Bromo-phenyl)-[6-(1H-indol-3-yl)-6H-phenanthridin-5-yl]-methanone was prepared from phenanthridine, 3-bromobenzoyl chloride, and indole according to GP 2. Yield, 22%. $^1$H-NMR (DMSO-d$_6$): δ=6.22 (d, J=1.9 Hz, 1H), 6.41 (s, br., 1H), 6.86 (t, J=7.5 Hz, 1H), 6.99-7.28 (m, 7H), 7.40-7.48 (m, 2H), 7.51-7.60 (m, 3H), 7.84 ("d", J=7 Hz, 1H), 7.98 (dd, J=7.9 Hz, J=1.1 Hz, 1H), 8.12 (d, J=7.5 Hz, 1H), 10.71 (s, 1H); (+)-ESI-MS: m/z=479 [M($^{79}$Br)+H]$^+$, 362[M($^{79}$Br)-indole+H]$^+$.

Example 14

[6-(1H-Indol-3-yl)-6H-phenanthridin-5-yl]-(3-trifluoromethyl-phenyl)-methanone was prepared from phenanthridine, 3-trifluoromethylbenzoyl chloride, and indole according to GP 2. Yield, 3%. $^1$H-NMR (DMSO-d$_6$): δ=6.24 (d, J=1.9 Hz, 1H), 6.38 (s, br., 1H), 6.82 (t, J=7.5 Hz, 1H), 7.01-7.10 (m, 2H), 7.15 (t, J=7.6 Hz, 1H), 7.20-7.32 (m, 2H), 7.40-7.60 (m, 6H), 7.74 (d, J=7.3 Hz, 1H), 7.88 (d, br., J=7 Hz, 1H), 8.00 (d, J=7.6 Hz, 1H), 8.13 (d, J=7.6 Hz, 1H), 10.73 (s, 1H); (+)-ESI-MS: m/z=469 [M+H]$^+$, 352 [M-indole+H]$^+$; (−)-ESI-MS: m/z=467 (M−H)$^-$.

Example 15

[6-(1H-Indol-3-yl)-6H-phenanthridin-5-yl]-(3-trifluoromethoxy-phenyl)-methanone was prepared from phenanthridine, 3-(trifluoromethoxy)benzoyl chloride, and indole according to GP 2. Yield, 16%. $^1$H-NMR (DMSO-d$_6$): δ=6.22 (d, J=2.0 Hz, 1H), 6.37 (s, br., 1H), 6.83 (t, J=7.5 Hz, 1H), 6.99-7.32 (m, 7H), 7.35-7.48 (m, 3H), 7.51-7.59 (m, 2H), 7.85 ("d", J≈7 Hz, 1H), 7.98 (dd, J=7.8 Hz, J=1.0 Hz, 1H), 8.12 (d, J=7.6 Hz, 1H), 10.72 (s, 1H); (+)-ESI-MS: m/z=485 [M+H]$^+$, 368 [M-indole+H]$^+$; (−)-ESI-MS: m/z=483 (M−H)$^-$.

Example 16

(2,4-Difluoro-phenyl)-[6-(1H-indol-3-yl)-6H-phenanthridin-5-yl]-methanone was prepared from phenanthridine, 2,4-difluorobenzoyl chloride, and indole according to GP 2. Yield, 25%. $^1$H-NMR (DMSO-d$_6$): δ=6.18 (d, br., J=1.4 Hz, 1H), 6.34 (d, br., J≈5 Hz, 1H), 6.82 (t, J≈7 Hz, 1H), 6.99-7.18 (m, 5H), 7.23-7.28 (m, 1H), 7.32 (s, br., 1H), 7.39-7.59 (m, 4H), 7.85 (s, br., 1H), 7.94 (dd, J=7.9 Hz, J=1.2 Hz, 1H), 8.07 (d, J=7.6 Hz, 1H), 10.71 (s, 1H); (+)-ESI-MS: m/z=437 [M+H]$^+$, 320 [M-indole+H]$^+$.

Example 17

(3,5-Bis-trifluoromethyl-phenyl)-[6-(1H-indol-3-yl)-6H-phenanthridin-5-yl]-methanone was prepared from phenanthridine, 3,5-bis(trifluoromethyl)benzoyl chloride, and indole according to GP 2. Yield, 8%. $^1$H-NMR (CD$_3$OD): δ=6.22 (d, J=0.8 Hz, 1H), 6.29 (s, br., 1H), 6.79 (t, J=7.5 Hz, 1H), 7.05-7.14 (m, 2H), 7.16-7.27 (m, 2H), 7.37 (s, br., 1H), 7.42-7.52 (m, 2H), 7.58 ("t", J≈7.3 Hz, 1H), 7.77 (s, br., 2H), 7.96 (s, br., 1H), 7.99 (dd, J=7.8 Hz, J=1.2 Hz, 2H), 8.12 (d, J=7.9 Hz, 1H); (+)-ESI-MS: m/z=537 [M+H]$^+$, 420 [M-indole+H]$^+$; (−)-ESI-MS: m/z=535 (M−H)$^-$.

Example 18

(2-Bromo-5-methoxy-phenyl)-[6-(1H-indol-3-yl)-6H-phenanthridin-5-yl]-methanone was prepared from phenanthridine, 2-bromo-5-methoxybenzoyl chloride, and indole according to GP 2. Yield, 30%. (+)-ESI-MS: m/z=509 [M($^{79}$Br)+H]$^+$, 392 [M($^{79}$Br)-indole+H]$^+$.

Example 19

[6-(1H-Indol-3-yl)-6H-phenanthridin-5-yl]-(2-trifluoromethoxy-phenyl)-methanone was prepared from phenanthridine, 2-(trifluoromethoxy)benzoyl chloride, and indole according to GP 2. Yield, 31%. $^1$H-NMR (DMSO-d$_6$): δ=6.16 (s, br., 1H), 6.25 (d, J=7.9 Hz, 1H), 6.72 (t, J=7.6 Hz, 1H), 7.00-7.12 (m, 4H), 7.23-7.29 (m, 1H), 7.36 (s, br., 1H), 7.37-7.59 (m, 6H), 7.85-7.95 (m, 2H), 8.05 (d, J=7.5 Hz, 1H), 10.68 (s, 1H); (+)-ESI-MS: m/z=485 [M+H]$^+$, 368 [M-indole+H]$^+$; (−)-ESI-MS: m/z=483 (M−H)$^-$.

Example 20

(6-Chloro-pyridin-3-yl)-[6-(1H-indol-3-yl)-6H-phenanthridin-5-yl]-methanone was prepared from phenanthridine, 6-chloronicotinoyl chloride, and indole according to GP 2. Yield, 55%. $^1$H-NMR (DMSO-d$_6$): δ=6.24 (d, J=1.7 Hz, 1H), 6.46 (s, br., 1H), 6.90 (t, J=7.5 Hz, 1H), 6.99-7.09 (m, 2H), 7.15-7.28 (m, 3H), 7.40-7.48 (m, 2H), 7.51-7.59 (m, 2H), 7.64 (d, J=8.2 Hz, 1H), 7.85 (d, J≈7 Hz, 1H), 8.01 (d, J=7.6 Hz, 1H), 8.12 (d, J=7.6 Hz, 1H), 8.23 (s, 1H), 10.73 (s, 1H); (+)-ESI-MS: m/z=436 [M($^{35}$Cl)+H]$^+$, 319 [M($^{35}$Cl)-indole+H]$^+$.

Example 21

(2-Chloro-pyridin-3-yl)-[6-(1H-indol-3-yl)-6H-phenanthridin-5-yl]-methanone was prepared from phenanthridine, 2-chloronicotinoyl chloride, and indole according to GP 2. Yield, 55%. $^1$H-NMR (DMSO-$d_6$): δ=6.18 (s, br., 1H), 6.37 (d, J=7.9 Hz, 1H), 6.79 (t, J≈7 Hz, 1H), 7.01-7.17 (m, 4H), 7.23-7.30 (m, 1H), 7.36-7.62 (m, 5H), 7.88 (s, br., 1H), 7.94 (d, J=7.7 Hz, 1H), 8.07 (d, J=7.1 Hz, 1H), 8.37 (d, J=4.6 Hz, J=1.3 Hz, 1H), 10.72 (s, 1H); (+)-ESI-MS: m/z=436 [M($^{35}$Cl)+H]$^+$, 319 [M($^{35}$Cl)-indole+H]$^+$.

Example 22

{6-[1-(2-Chloro-pyridine-3-carbonyl)-1-indol-3-yl]-6H-phenanthridin-5-yl}-(2-chloro-pyridin-3-yl)-methanone was obtained as a side product from the synthesis of (2-chloro-pyridin-3-yl)-[6-(1H-indol-3-yl)-6H-phenanthridin-5-yl]-methanone. Yield, 8%. (+)-ESI-MS: m/z=575 [M($^{35}$Cl$_2$)+H]$^+$, 319 [M($^{35}$Cl)-acylindole+H]$^+$.

Example 23

Furan-2-yl-[6-(1H-indol-3-yl)-6H-phenanthridin-5-yl]-methanone was prepared from phenanthridine, 2-furoyl chloride, and indole according to GP 2. Yield, 72%. $^1$H-NMR (DMSO-$d_6$): δ=6.19 ("d", J=2.1 Hz, 1H), 6.51 (dd, J=3.4 Hz, J=1.7 Hz, 1H), 6.61 (d, J=7.9 Hz, 1H), 6.71 (d, J=3.4 Hz, 1H), 6.95-7.08 (m, 3H), 7.17-7.27 (m, 2H), 7.41 ("t", J≈7.5 Hz, 1H), 7.48-7.56 (m, 2H), 7.63-7.65 (m, 2H), 7.88 (d, J=7.0 Hz, 1H), 7.97 (d, J=7.9 Hz, 1H), 8.07 (d, J=7.8 Hz, 1H), 10.70 (s, 1H); (+)-ESI-MS: m/z=391 [M+H]$^+$, 274 [M-indole+H]$^+$.

Example 24

[6-(1H-Indol-3-yl)-6H-phenanthridin-5-yl]-thiophen-2-yl-methanone was prepared from phenanthridine, 2-thenoyl chloride, and indole according to GP 2. Yield, 17%. $^1$H-NMR (CD$_3$OD): δ=6.17 (d, J=0.9 Hz, 1H), 6.67 (d, J=7.9 Hz, 1H), 6.84-6.89 (m, 2H), 6.91 (td, J=3.8 Hz, J=1.1 Hz, 1H), 7.02-7.11 (m, 2H), 7.18-7.24 (m, 2H), 7.26 (s, 1H), 7.38-7.46 (m, 2H), 7.50-7.56 (m, 2H), 7.93 (dd, J=7.9 Hz, J=1.3 Hz, 1H), 7.97-8.01 (m, 1H), 8.06 (d, J=7.9 Hz, 1H); (+)-ESI-MS: m/z=407 [M+H]$^+$, 290 [M-indole+H]$^+$.

Example 25

(2,5-Dimethyl-2H-pyrazol-3-yl)-[6-(1H-indol-3-yl)-6H-phenanthridin-5-yl]-methanone was prepared from phenanthridine, 1,3-dimethylpyrazole-5-carbonyl chloride, and indole according to GP 2. Yield, 7%. $^1$H-NMR (DMSO-$d_6$): δ=1.97 (s, 3H), 3.77 (s, 3H), 5.56 (s, 1H), 6.20 (s, 1H), 6.63 (s, br., 1H), 6.95 (t, J=7.5 Hz, 1H), 6.99-7.10 (m, 2H), 7.14-7.30 (m, 3H), 7.42 (t, J≈7.2 Hz, 1H), 7.49-7.58 (m, 2H), 7.83 (d, J=6.7 Hz, 1H), 7.98 (d, J=7.6 Hz, 1H), 8.09 (d, J=7.6 Hz, 1H), 10.72 (s, 1H); (+)-ESI-MS: m/z=419 [M+H]$^+$, 302 [M-indole+H]$^+$.

Example 26

1-[6-(1H-Indol-3-yl)-6H-phenanthridin-5-yl]-2-methyl-propan-1-one was prepared from phenanthridine, isobutyryl chloride, and indole according to GP 2. Yield, 18%. (+)-ESI-MS: m/z=367 [M+H]$^+$, 250 [M-indole+H]$^+$, 180.

Example 27

1-[6-(1-Isobutyryl-1H-indol-3-yl)-6H-phenanthridin-5-yl]-2-methyl-propan-1-one was obtained as a side product from the synthesis of 1-[6-(1H-indol-3-yl)-6H-phenanthridin-5-yl]-2-methyl-propan-1-one. Yield, 23%. (+)-ESI-MS: m/z=437 [M+H]$^+$, 250 [M-acylindole+H]$^+$, 180.

Example 28

1-[6-(1H-Indol-3-yl)-6H-phenanthridin-5-yl]-2-methyl-pentan-1-one was prepared from phenanthridine, 2-methylvaleryl chloride, and indole according to GP 2.

Yield, 6%. $^1$H-NMR (DMSO-$d_6$): δ=0.53-0.80 (m, 3H), 0.88-1.13 (m, 2H), 1.22 (d, J=6.5 Hz, 3H), 1.29-1.47 (m, 2H), 2.99-3.12 (m, 1H), 6.08 (s, br., 1H), 6.94-7.08 (m, 3H), 7.16 (td, J=7.8 Hz, J=1.5 Hz, 1H), 7.20-7.31 (m, 3H), 7.34-7.52 (m, 3H), 7.68 (d, J=7.2 Hz, 1H), 7.94 (d, J=7.5 Hz, 1H), 8.01 (d, J=7.2 Hz, 1H), 10.61 (s, 1H); (+)-ESI-MS: m/z=395 [M+H]$^+$, 278 [M-indole+H]$^+$.

Example 29

1-[6-(1H-Indol-3-yl)-6H-phenanthridin-5-yl]-nonan-1-one was prepared from phenanthridine, pelargonyl chloride, and indole according to GP 2. Yield, 2%. $^1$H-NMR (DMSO-$d_6$): δ=0.81 (t, J=7.0 Hz, 3H), 0.99-1.24 (m, 10H), 1.44-1.58 (m, 2H), 2.30-2.75 (m, 2H; overlap with solvent signal), 6.08 (s, br., 1H), 6.98 (td, J=7.4 Hz, 1H), 7.04 (td, J=7.4 Hz, 1H), 7.10-7.19 (m, 2H), 7.20-7.33 (m, 3H), 7.38 (td, J=7.3 Hz, J=1.0 Hz, 1H), 7.43-7.51 (m, 2H), 7.69 (d, J=7.5 Hz, 1H), 7.94 (d, J=7.6 Hz, 1H), 8.00 (d, J=7.4 Hz, 1H), 10.62 (s, 1H); (+)-ESI-MS: m/z=437 [M+H]$^+$, 320 [M-indole+H]$^+$, 180.

Example 30

Cyclobutyl-[6-(1H-indol-3-yl)-6H-phenanthridin-5-yl]-methanone was prepared from phenanthridine, cyclobutanecarboxylic acid chloride, and indole according to GP 2. Yield, 11%. $^1$H-NMR (DMSO-$d_6$): δ=1.48-1.62 (m, 1H), 1.65-2.02 (m, 3H), 2.15-2.41 (m, 2H), 3.49-3.66 (m, 1H), 6.07 (s, br., 1H), 6.92-7.07 (m, 3H), 7.16 (t, J≈7.5 Hz, 1H), 7.19-7.30 (m, 3H), 7.35-7.42 (m, 1H), 7.43-7.52 (m, 2H), 7.68 (d, J=6.7 Hz, 1H), 7.92 (d, J=7.4 Hz, 1H), 8.01 (d, J=7.3 Hz, 1H), 10.62 (s, 1H); (+)-ESI-MS: m/z=379 [M+H]$^+$, 262 [M-indole+H]$^+$, 180.

Example 31

Cyclopentyl-[6-(1H-indol-3-yl)-6H-phenanthridin-5-yl]-methanone was prepared from phenanthridine, cyclopentanecarboxylic acid chloride, and indole according to GP 2. Yield, 10%. $^1$H-NMR (DMSO-$d_6$): δ=1.28-1.43 (m, 2H), 1.47-1.75 (m, 4H), 1.90-2.04 (m, 2H), 3.14-3.26 (m, 1H), 6.07 (s, br., 1H), 6.95-7.10 (m, 3H), 7.16 (td, J=7.6 Hz, J=1.6 Hz, 1H), 7.20-7.31 (m, 3H), 7.35-7.42 (m, 1H), 7.44-7.52 (m, 2H), 7.66 (d, J=7.4 Hz, 1H), 7.93 (d, J=7.4 Hz, 1H), 8.01 (d, J=7.5 Hz, 1H), 10.61 (s, 1H); (+)-ESI-MS: m/z=393 [M+H]$^+$, 276 [M-indole+H]$^+$, 180.

Example 32

Cyclohexyl-[6-(1H-indol-3-yl)-6H-phenanthridin-5-yl]-methanone was prepared from phenanthridine, cyclohexanecarboxylic acid chloride, and indole according to GP 2. Yield, 7%. (+)-ESI-MS: m/z=407 [M+H]$^+$, 290 [M-indole+H]$^+$, 180.

Example 33

3-Cyclopentyl-1-[6-(1H-indol-3-yl)-6H-phenanthridin-5-yl]-propan-1-one was prepared from phenanthridine, 3-cyclopentylpropionyl chloride, and indole according to GP 2. Yield, 5%. $^1$H-NMR (CD$_3$OD): δ=0.80-0.99 (m, 2H), 1.27-1.70 (m, 9H), 2.60 ("t", J≈7 Hz, 2H), 6.08 (s, 1H), 6.98-7.04 (m, 2H), 7.07 (td, J≈7 Hz, J=1.3 Hz, 1H), 7.12 (td, J=7.9 Hz, J=1.4 Hz, 1H), 7.21 ("d", J≈7.4 Hz, 1H), 7.26 ("t", J≈7.6 Hz, 1H), 7.36-7.42 (m, 3H), 7.45-7.52 (m, 1H), 7.78 (d, J=7.3 Hz, 1H), 7.90 (d, J=7.7 Hz, 1H), 7.97 (d, J=7.7 Hz, 1H); (+)-ESI-MS: m/z=421 [M+H]$^+$, 304 [M-indole+H]$^+$, 180.

Example 34

3-Cyclohexyl-1-[6-(1H-indol-3-yl)-6H-phenanthridin-5-yl]-propan-1-one was prepared from phenanthridine, 3-cyclohexylpropionyl chloride, and indole according to GP 2. Yield, 5.5%. $^1$H-NMR (CD$_3$OD): δ=0.56-0.79 (m, 2H), 0.86-1.09 (m, 4H), 1.26-1.62 (m, 7H), 2.47-2.70 (m, 2H), 6.08 (s, 1H), 6.96-7.05 (m, 2H), 7.07 (td, J=7.2 Hz, J=1.3 Hz, 1H), 7.13 (td, J=7.9 Hz, J=1.4 Hz, 1H), 7.21 ("d", J≈7.4 Hz, 1H), 7.27 ("t", J≈7.6 Hz, 1H), 7.36-7.42 (m, 3H), 7.46-7.53 (m, 1H), 7.78 (d, J=7.5 Hz, 1H), 7.90 (d, J=7.6 Hz, 1H), 7.98 (d, J=7.7 Hz, 1H); (+)-ESI-MS: m/z=435 [M+H]$^+$, 318 [M-indole+H]$^+$, 180.

Example 35

1-[6-(1H-Indol-3-yl)-6H-phenanthridin-5-yl]-3-phenyl-propan-1-one was prepared from phenanthridine, hydrocinnamoyl chloride, and indole according to GP 2.

Yield, 9%. $^1$H-NMR (CD$_3$OD): δ=2.74-3.01 (m, 4H), 6.05 (s, 1H), 6.80 (d, J=7.9 Hz, 1H), 6.92-7.10 (m, 8H), 7.17-7.26 (m, 2H), 7.32-7.40 (m, 3H), 7.43-7.51 (m, 1H), 7.78 (dd, J=7.1 Hz, J=1.0 Hz, 1H), 7.85 (dd, J=7.9 Hz, J=1.0 Hz, 1H), 7.92 (d, J=7.7 Hz, 1H); (+)-ESI-MS: m/z=429 [M+H]$^+$, 312 [M-indole+H]$^+$, 180.

Example 36

6-(1H-Indol-3-yl)-6H-phenanthridine-5-carboxylic acid methyl ester was prepared from phenanthridine, methyl chloroformate, and indole according to GP 2. Yield, 9%. (+)-ESI-MS: m/z=355 [M+H]$^+$, 238 [M-indole+H]$^+$.

Example 37

[6-(1H-Indol-3-yl)-6H-phenanthridin-5-yl]-oxo-acetic acid methyl ester was prepared from phenanthridine, methyl oxalyl chloride, and indole according to GP 2.

Yield, 2%. $^1$H-NMR (DMSO-d$_6$): δ=3.66 (s, 3H), 6.18 (d, J≈2 Hz, 1H), 6.84 (dd 7.9 Hz, J=0.9 Hz, 1H), 7.00-7.11 (m, 2H), 7.14 (s, 1H), 7.17 (td, J=7.9 Hz, J=1.2 Hz, 1H), 7.27 (d, J=7.0 Hz, 1H), 7.33 ((td, J=7.6 Hz, J=1.0 Hz, 1H), 7.44 (td, J=7.4 Hz, J=1.0 Hz, 1H), 7.51-7.58 (m, 2H), 7.65 (d, J=7.5 Hz, 1H), 8.04 (dd, J=7.9 Hz, J=1.1 Hz, 1H), 8.09 (dd, J=8.0 Hz, J=1.1 Hz, 1H), 10.77 (s, 1H); (+)-ESI-MS: m/z=383 [M+H]$^+$, 266 [M-indole+H]$^+$.

Example 38

6-(1H-Indol-3-yl)-6H-phenanthridine-5-carboxylic acid ethyl ester was prepared from phenanthridine, ethyl chloroformate, and indole according to GP 2. Yield, 50%. (+)-ESI-MS: m/z=369 [M+H]$^+$, 252 [M-indole+H]$^+$.

Example 39

[6-(1H-Indol-3-yl)-6H-phenanthridin-5-yl]-oxo-acetic acid ethyl ester was prepared from phenanthridine, ethyl oxalyl chloride, and indole according to GP 2. Yield, 2%. $^1$H-NMR (DMSO-d$_6$): δ=1.04 (t, J=7.1 Hz, 3H), 4.12 (q, J=7.1 Hz, 2H), 6.19 (dd, J=2.4 Hz, J=0.6 Hz, 1H), 6.87 (dd, J=7.9 Hz, J=0.9 Hz, 1H), 7.01-7.11 (m, 2H), 7.13 (s, 1H), 7.17 (td, J=7.9 Hz, J=1.3 Hz, 1H), 7.27 (d, J=7.0 Hz, 1H), 7.33 (td, J=7.5 Hz, J=1.0 Hz, 1H), 7.43 (td, J=7.4 Hz, J=1.0 Hz, 1H), 7.50-7.58 (m, 2H), 7.66 (d, J=7.5 Hz, 1H), 8.05 (dd, J=7.8 Hz, J=1.1 Hz, 1H), 8.09 (dd, J=8.0 Hz, J=1.3 Hz, 1H), 10.76 (s, 1H); (+)-ESI-MS: m/z=397 [M+H]$^+$, 280 [M-indole+H]$^+$.

Example 40

Furan-2-yl-[6-(1H-pyrrol-2-yl)-6H-phenanthridin-5-yl]-methanone was prepared from phenanthridine, 2-furoyl chloride, and pyrrole according to GP 2. Yield, 25%. $^1$H-NMR (DMSO-d$_6$): δ=5.16 (s, 1H), 5.68 (q, J=2.7 Hz, 1H), 6.52-6.59 (m, 2H), 6.74 (s, 1H), 6.78 (d, J=3.3 Hz, 1H), 6.91 (d, J=7.8 Hz, 1H), 7.11 (td, J=7.7 Hz, J=1.1 Hz, 1H), 7.22 (td, J=7.5 Hz, J=1.2 Hz, 1H), 7.39 (td, J=7.4 Hz, J=0.9 Hz, 1H), 7.44-7.54 (m, 2H), 7.68 (s, 1H), 7.91 (dd, J=7.9 Hz, J=1.1 Hz, 1H), 8.00 (d, J=7.6 Hz, 1H), 10.61 (s, 1H); (+)-ESI-MS: m/z=274 [M-pyrrole]$^+$.

Example 41

(6-{5-[5-(Furan-2-carbonyl)-5,6-dihydro-phenanthridin-6-yl]-1H-pyrrol-2-yl}-6H-phenanthridin-5-yl)-furan-2-yl-methanone was obtained as a side product from the synthesis of furan-2-yl-[6-(1H-pyrrol-2-yl)-6H-phenanthridin-5-yl]-methanone. Yield, 8.8%. (+)-ESI-MS: m/z=274 (fragment).

Example 42

(3,5-Bis-trifluoromethyl-phenyl)-[6-(1H-pyrrol-2-yl)-6H-phenanthridin-5-yl]-methanone was prepared from phenanthridine, 3,5-bis(trifluoromethyl)benzoyl chloride, and pyrrole according to GP 2. Yield, 12.5%. $^1$H-NMR (DMSO-d$_6$): δ=5.21 (s, 1H), 5.79 (q, J=2.8 Hz, 1H), 6.59-6.63 (m, 1H), 6.64 (s, br., 1H), 6.84-7.09 (m, br., 2H), 7.21 (t, J=7.5 Hz, 1H), 7.43 (t, J=7.3 Hz, 1H), 7.51 (t, J≈7 Hz, 1H), 7.57 (d, J=7.1 Hz, 1H), 7.86 (s, br., 2H), 7.96 (d, J=7.8 Hz, 1H), 8.08 (d, J=7.5 Hz, 1H), 8.19 (s, 1H), 10.66 (s, 1H); (+)-ESI-MS: m/z=420 [M-pyrrole]$^+$.

Example 43

(6-{5-[5-(3,5-Bis-trifluoromethyl-benzoyl)-5,6-dihydro-phenanthridin-6-yl]-1H-pyrrol-2-yl}-6H-phenanthridin-5-yl)-(3,5-bis-trifluoromethyl-phenyl)-methanone was obtained as a side product from the synthesis of (3,5-bis-trifluoromethyl-phenyl)-[6-(1H-pyrrol-2-yl)-6H-phenanthridin-5-yl]-methanone. Yield, 7.1%. $^1$H-NMR (DMSO-d$_6$): δ=4.80 (d, J=1.9 Hz, 2H), 6.51 (s, br., 2H), 6.92 (s, br., 4H), 7.18 (t, J=7.5 Hz, 2H), 7.37 (t, J=7.2 Hz, 2H), 7.46 (t, J=7.5 Hz, 2H), 7.53 (d, J=7.0 Hz, 2H), 7.84 (s, br., 4H), 7.90 (d, J=7.8 Hz, 2H), 8.02 (d, J=7.7 Hz, 2H), 8.19 (s, 2H), 10.58 (s, 1H); (+)-ESI-MS: m/z=420 (fragment).

Example 44

2-(5-Acetyl-5,6-dihydro-phenanthridin-6-yl)-cyclopentanone was prepared from phenanthridine, acetyl chloride, and 1-(trimethylsilyloxy)cyclopentene according to GP 2. Yield, 25%. $^1$H-NMR (DMSO-$d_6$): δ=1.23-1.38 (m, 2H), 1.43-1.61 (m, 1H), 1.67-1.81 (m, 1H), 1.81-2.27 (m, 6H), 6.15 (s, 1H), 7.21-7.56 (m, 6H), 7.85-7.97 (m, 2H); (+)-ESI-MS: m/z=306 [M+H]$^+$, 222, 180.

Example 45

(5-Acetyl-5,6-dihydro-phenanthridin-6-yl)-acetic acid methyl ester was prepared from phenanthridine, acetyl chloride, and 1-(tert-butyldimethylsilyloxy)-1-methoxyethene according to GP 2. Yield, 43%. $^1$H-NMR (DMSO-$d_6$): δ=2.12 (s, br., 3H), 2.28-2.43 (m, 2H), 3.54 (s, 3H), 6.22 (s, br., 1H), 7.28-7.56 (m, 6H), 7.90-7.98 (m, 2H); (+)-ESI-MS: m/z=296 [M+H]$^+$, 254, 222, 180.

Example 46

(5-Acetyl-5,6-dihydro-phenanthridin-6-yl)-acetic acid. To a solution of (5-acetyl-5,6-dihydro-phenanthridin-6-yl)-acetic acid methyl ester (210 mg, 0.71 mmol) dissolved in a mixture of dioxane (10 mL) and water (10 mL), LiOH×H$_2$O (42 mg, 1 mmol) was added. The solution was allowed to stir at r.t. for 4 h. Citric acid (5% solution in water) was added and the mixture was extracted with ethyl acetate. The organic phase was washed with citric acid (2×), water (1×), and brine (1×). After drying over MgSO$_4$, the solvent was removed in vacuo to give a colourless oil that solidified on standing ar r.t. Yield, 70%. (+)-ESI-MS: m/z=282 [M+H]$^+$, 240, 222, 180.

Example 47

[5-(3,5-Bis-trifluoromethyl-benzoyl)-5,6-dihydro-phenanthridin-6-yl]-acetic acid methyl ester was prepared from phenanthridine, 3,5-bis(trifluormethyl)benzoyl chloride, and 1-(tert-butyldimethylsilyloxy)-1-methoxyethene according to GP 2. Yield, 49%. $^1$H-NMR (DMSO-$d_6$): δ=2.46 (dd, J=14.5 Hz, J=7.0 Hz, 1H), 2.57 (dd, J=14.5 Hz, J=7.8 Hz, 1H), 3.57 (s, 3H), 6.03 (s, br., 1H), 6.80 (s, br., 1H), 7.12 (s, br., 1H), 7.31 (t, J=7.6 Hz, 1H), 7.36-7.44 (m, 2H), 7.46-7.53 (m, 1H), 7.80 (s, br., 2H), 8.03 (dd, J=7.9 Hz, J=1.1 Hz, 1H), 8.07 (d, J=7.8 Hz, 1H), 8.20 (s, br., 1H); (+)-ESI-MS: m/z=494 [M+H]$^+$.

Example 48

[5-(3,5-Bis-trifluoromethyl-benzoyl)-5,6-dihydro-phenanthridin-6-yl]-acetic acid was prepared from [5-(3,5-bis-trifluoromethyl-benzoyl)-5,6-dihydro-phenanthridin-6-yl]-acetic acid methyl ester following the procedure described in Example 46. Yield, 90%. $^1$H-NMR (DMSO-$d_6$): δ=2.34 (dd, J=15.1 Hz, J=7.2 Hz, 1H), 2.54 (dd, J=15.1 Hz, J=7.5 Hz, 1H), 6.05 (s, br., 1H), 6.73 (s, br., 1H), 7.16 (s, br., 1H), 7.27-7.44 (m, 3H), 7.45-7.53 (m, 1H), 7.82 (s, br., 2H), 8.05 ("t", J=8 Hz, 2H), 8.20 (s, br., 1H), 12.41 (s, br., 1H); (+)-ESI-MS: m/z=480 [M+H]$^+$; (−)-ESI-MS: m/z=478 [M−H]$^-$.

Example 49

(6-Benzo[1,3]dioxol-5-yl-6H-phenanthridin-5-yl)-(3,5-bis-trifluoromethyl-phenyl)-methanone. Step 1: Preparation of 6-benzo[1,3]dioxol-5-yl-5,6-dihydro-phenanthridine. Phenanthridine (358 mg, 2.0 mmol) was dissolved in dry THF (2.5 mL) in a Schlenk tube under argon and 3,4-(methylenedioxy)phenylmagnesium bromide (4.0 mmol) was added. The solution was stirred at 65° C. for 4.5 h, then water was added. The pH was adjusted between 6 and 7 using diluted hydrochlorid acid and then the mixture was extracted several times with ethyl acetate. The combined organic phases were washed with brine. After drying over Na$_2$SO$_4$, the solvent was removed in vacuo. The residue was chromatographed on silica gel using a petroleum ether/ethyl acetate gradient to yield the product (yellowish solid, 365 mg, 61%). $^1$H-NMR (DMSO-$d_6$): δ=5.47 (s, 1H), 5.92 (s, 2H), 6.57 (s, 1H), 6.62-6.76 (m, 3H), 6.78 (d, J=8.0 Hz, 1H), 6.82 (d, J=1.5 Hz, 1H), 7.00-7.07 (m, 2H), 7.18 (td, J=7.5 Hz, J=1.1 Hz, 1H), 7.29 (td, J=7.5 Hz, J=1.3 Hz, 1H), 7.69 (d, J=7.6 Hz, 1H), 7.78 (d, J=8.0 Hz, 1H); (+)-ESI-MS: m/z=302 [M+H]$^+$, 180. Step 2: Preparation of (6-benzo[1,3]dioxol-5-yl-6H-phenanthridin-5-yl)-(3,5-bis-trifluoromethyl-phenyl)-methanone. To a solution of 6-benzo[1,3]dioxol-5-yl-5,6-dihydro-phenanthridine (69 mg, 0.23 mmol) in dry THF (1 mL), triethylamine (40 μL, 0.28 mmol) was added followed by 3,5-bis(trifluormethyl)benzoyl chloride (46 μL, 0.25 mmol). The mixture was allowed to stir at r.t. for 0.5 h. Additional triethylamine (16 μL, 0.11 mmol) and 3,5-bis(trifluormethyl)benzoyl chloride (12 μL, 0.07 mmol) were added. After stirring for 0.5 h at r.t., the mixture was chromatographed on silica gel using a petroleum ether/ethyl acetate gradient to yield the product (colourless oil, 90 mg, 73%). $^1$H-NMR (DMSO-$d_6$): δ=5.91 (s, 2H), 6.42 (d, J=8.1 Hz, 1H), 6.68 (d, J=8.1 Hz, 1H), 6.76 (s, 1H), 6.75-7.04 (m, 3H), 7.19 (t, J=7.5 Hz, 1H), 7.47 (t, J=7.4 Hz, 1H), 7.55 (t, J=7.4 Hz, 1H), 7.60 (d, J=7.4 Hz, 1H), 7.44 (s, 2H), 7.98 (d, J=7.6 Hz, 1H), 8.09-8.18 (m, 2H).

Example 50

5-(Toluene-4-sulfonyl)-5,6-dihydro-dibenzo[b,d]azepin-7-one was synthesized as described by W. Paterson, G. R. Proctor, *J. Chem. Soc.* 1962, 3468-3472.

Example 51

Influence of Compounds According to the Invention on Keratinocyte Proliferation $5 \times 10^3$ HaCaT keratinocytes were seeded into 60 wells of 96 well plates in 200 μl KBM/10% FCS and incubated for 24 hrs at 37° C. The test compounds were dissolved at 100 mM in DMSO. The test items were then diluted to a concentration of 25 μM in KBM/FCS with a final concentration of 1% DMSO. The test compounds, as well as the negative control for unstimulated cells (KBM/1% DMSO) and stimulated cells (KBM/FCS/1% DMSO), were added to the HaCaTs in triplicates and incubated for 48 hrs. At the end of the incubation period, the media was removed and cell numbers were determined with Cell Titer Viability Assay from Promega (#G7571/G7572) according to the manufacturer's instructions. Compounds according to Examples 3, 6, 7, 11, 12, 14, 17, 20, 21, 23, 26, 28, 34, 35 and 50 as test compounds resulted in an inhibition of keratinocyte proliferation of more than 50% compared to control experiments.

Thus, the compounds of formula I, formula II, formula III or formula IV are suitable for treating skin diseases or skin diseases associated with abnormal cell proliferation.

Example 52

Influence of Compounds According to Formula I to IV on T Cell Proliferation

Peripheral blood mononuclear cells (PBMCs) were isolated from peripheral blood by Ficoll gradient centrifugation. $1\times10^6$ PBMCs/ml were resuspended in RPMI/10% fetal calf serum (FCS) and were activated with 10 μg/ml soluble anti-CD3-antibody for 2 days. Subsequently, the cells were washed three times with PBS gewaschen and were resuspended in 96-well plates in a concentration of $2\times10^5$ cells/well. The cells were preincubated with test compound (containing DMSO in a final concentration of 0,1%) for 1 hour, and were then again stimulated with 10 μg/ml soluble anti-CD3-antibody. As positive and negative controls, PBMCs, stimulated with soluble anti-CD3-, and non-stimulated PBMCs plus 0,1% DMSO were used. The addition of 0,1% DMSO had no effect on the proliferation rate. After another 2 days of incubation, the cells were incubated with 1 μCi per well [$^3$H]-Thymidin for 18 hours. The cells were harvested using a Mikro 96 Harvester (Skatron Instruments, Lier, Norwegen). The cpm-values indicative for proliferation were determined using a Packard Matrix 9600 Counter (Canberra Packard, Schwadorf, Österreich). The experiments were made with three different human donors.

In order to determine the $EC_{50}$ of test compounds, the value of anti-CD3-stimulated cells plus 0,1% DMSO was set as 100%. All other values were divided by the 100% value in order to obtain a relative percentage of inhibition. The obtained percentage values were used to dertermine the $EC_{50}$ values using Sigma Plot. The $EC_{50}$ of compound of Example 3 was below 25 μM.

Thus, the compounds of formula I, formula II, formula III or formula IV are suitable for treating inflammatory diseases or diseases associated with T cells.

What is claimed is:

1. A compound of formula (II), or a pharmaceutically acceptable salt thereof,

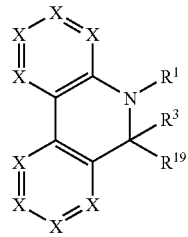

II wherein
X is C—$R^8$;
$R^1$ is independently $COR^{2'}$, $CO_2R^2$, $COCO_2R^2$, $SOR^2$, $SO_2R^2$, $C_2$-$C_6$-alkyl, cycloalkyl, alkoxy, —OH, —SH, alkylamine, alkylthio, hydroxyalkyl, haloalkyl, haloalkyloxy, aryl or heteroaryl;
$R^2$ is independently H, alkyl, cycloalkyl, —$NH_2$, alkylamine, aryl or heteroaryl;
$R^{2'}$ is independently $C_2$-$C_6$-alkyl, alkylamine, heteroaryl, or an aromatic group having five, or seven to fifteen carbon atoms, which can optionally be substituted by one or more substituents R', or a phenyl group substituted by one or more substituents R''', or a non-aromatic ring system containing three to eight carbon atoms, wherein one or more of the carbon atoms in the ring can be substituted by a group E, E being defined as S, O, NR', SO, or $SO_2$;
$R^3$ is independently H, halogen, $COR^2$, $CO_2R^2$, $SOR^2$, $SO_2R^2$, alkyl, cycloalkyl, alkoxy, alkylamine, —OH, —SH, alkylthio, hydroxyalkyl, haloalkyl, haloalkyloxy, aryl or heteroaryl, or $R^{19}$ is absent and $R^3$ is S forming a double bond with the carbon atom of the ring system to which it is attached;
$R^8$ is independently H, $COR^2$, $CO_2R^2$, $SOR^2$, $SO_2R^2$, alkyl, cycloalkyl, alkoxy, —$NH_2$, alkylamine, —$NR^{11}COR^2$, halogen, —OH, —SH, alkylthio, hydroxyalkyl, haloalkyl, haloalkyloxy, aryl or heteroaryl;
$R^{11}$ is independently H, alkyl, cycloalkyl, alkoxy, —OH, —SH, alkylthio, hydroxyalkyl, aryl, or heteroaryl;
$R^{19}$ is independently a polycyclic aromatic ring system, heteroaryl or cycloalkyl;
R' is independently H, —$CO_2R''$, —$CONHR''$, —$CR''O$, —$SO_2NR''$, —$NH_2$, —$NR^{11}COR^2$, —$NO_2$, —$NR^{11}$—$SO_2$-haloalkyl, —$NR^{11}$—$SO_2$-alkyl, —$SO_2$-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
R'' is independently H, —$NH_2$, haloalkyl, hydroxyalkyl, alkyl, cycloalkyl, aryl, heteroaryl or aminoalkyl;
R''' is independently —$CO_2R''$, —$CONHR''$, —$CR''O$, —$SO_2NR''$, —$NR''$—CO-haloalkyl, —$NO_2$, —$NR''$—$SO_2$-haloalkyl, —$NR''$—$SO_2$-alkyl, —$SO_2$-alkyl, —$NR''$—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
wherein a $C_2$-$C_6$-alkyl group denotes a linear or branched $C_2$-$C_6$-alkyl, a linear or branched $C_2$-$C_6$-alkenyl or a linear or branched $C_2$-$C_6$-alkinyl group, which can optionally be substituted by one or more substituents R';
wherein an alkyl group, if not stated otherwise, denotes a linear or branched $C_1$-$C_6$-alkyl, a linear or branched $C_2$-$C_6$-alkenyl or a linear or branched $C_2$-$C_6$-alkinyl group, which can optionally be substituted by one or more substituents $R^a$;
wherein $R^a$ is independently H, —$CO_2R^b$, —$CONHR^b$, —$CR^bO$, —$SO_2NR^b$, —$NR^b$—CO haloalkyl, —$NO_2$, —$NR^b$—$SO_2$-haloalkyl, —$NR^b$—$SO_2$-alkyl, —$SO_2$-alkyl, —$NR^b$—CO-alkyl,
CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
wherein $R^b$ is independently H, haloalkyl, hydroxyalkyl, alkyl, cycloalkyl, aryl, heteroaryl or aminoalkyl;
wherein a cycloalkyl group denotes a non-aromatic ring system containing three to eight carbon atoms, wherein one or more of the carbon atoms in the ring can be substituted by a group F, F being O, S, SO, $SO_2$, N, or NR'', R'' being as defined above;
wherein an alkoxy group denotes an O-alkyl group, the alkyl group being as defined above;
wherein an alkylthio group denotes an S-alkyl group, the alkyl group being as defined above;
wherein a haloalkyl group denotes an alkyl group which is substituted by one to five halogen atoms, the alkyl group being as defined above;
wherein a hydroxyalkyl group denotes an HO-alkyl group, the alkyl group being as defined above;
wherein a haloalkyloxy group denotes an alkoxy group which is substituted by one to five halogen atoms, the alkyl group being as defined above;
wherein a hydroxyalkylamino group denotes an (HO-alkyl)$_2$-N— group or HO-alkyl-NH— group, the alkyl group being as defined above;

wherein an alkylamino group denotes an HN-alkyl or N-dialkyl group, the alkyl group being as defined above;

wherein a halogen group is chlorine, bromine, fluorine or iodine;

wherein a polycyclic aromatic ring system denotes an aromatic ring system in which two or more aryl groups and/or heteroaryl groups are fused, which can optionally be substituted by one or more substituents R', where R' is as defined above;

wherein an aryl group denotes an aromatic group having five to fifteen carbon atoms, which can optionally be substituted by one or more substituents R', where R' is as defined above;

wherein a heteroaryl group denotes a 5- or 6-membered aryl heterocyclic group which contains at least one heteroatom O, N, or S and is optionally fused to another ring, and/or optionally substituted by one or more substituents R', wherein R' is as defined above.

2. The compound of claim 1, wherein the cycloalkyl group is a non-aromatic ring system containing four to eight carbon atoms.

3. The compound of claim 1, wherein the alkoxy group is a methoxy, ethoxy, isopropoxy, t-butoxy or pentoxy group.

4. The compound according to claim 1, wherein the heterocyclic group is fused to another ring.

5. The compound according to claim 1, wherein R' is $COR^{2'}$.

6. The compound according to claim 1, wherein $R^3$ is H.

7. The compound according to claim 1, wherein $R^8$ is H.

8. The compound according to claim 1, wherein $R^{19}$ is heteroaryl.

9. The compound according to claim 8, wherein $R^{19}$ is indoyl.

10. The compound according to claim 1, which is 1-[6-(1H-Indol-3-yl)-6H-phenanthridin-5-yl]-2-methyl-pentan-1-one.

11. The compound according to claim 1, which is (2,5-Dimethyl-2H-pyrazol-3-yl)-[6-(1H-indol-3-yl)-6H-phenanthridin-5-yl]-methenone.

12. The compound according to claim 1, which is 1-[6-(1-Indol-3-yl)-6H-phenanthridin-5-yl]-2-methyl-pentan-1-one.

13. The compound according to claim 1, which is cyclobutyl-[6-(1H-Indol-3-yl)-6H-phenanthridin-5-yl]-methanone.

14. The compound according to claim 1, which is [6-(1H-Indol-3-yl)-6H-phenanthridin-5-yl]-oxo-acetic acid methyl ester.

15. A compound of claim 2 wherein aryl or an aromatic group is phenyl, -o-$C_6H_4$—R', -m-$C_6H_4$—R', -p-$C_6H_4$—R', 1-naphthyl, 2-naphthyl, 1-anthracenyl or 2-anthracenyl;

heteroaryl is thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, 2-indolyl, 3-indolyl, 2-indolinyl, 3-indolinyl, benzo[b]furanyl, benzo[b]thiophenyl, benzimidazolyl, benzothiazolyl, quinazolinyl, quinoxazolinyl, quinolinyl, tetrahydroquinolinyl, isoquinolinyl, or tetraliydroisoquinolinyl;

a non-aromatic ring system is -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, or 1-alkylpiperazine-4-yl; and a polycyclic aromatic ring system is 1-naphthyl, 2-naphthyl, 1-anthracenyl or 2-anthracenyl.

* * * * *

UNITED STATES PATENT AND TRADEMARK OFFICE
CERTIFICATE OF CORRECTION

PATENT NO. : 7,276,606 B2
APPLICATION NO. : 11/118421
DATED : October 2, 2007
INVENTOR(S) : Stefano Pegoraro It is certified that error appears in the above-identified patent and that said Letters Patent is hereby corrected as shown below:

Column 41, line 67, reads "aryl or heteroaryl," should read --aryl, or heteroaryl--
Column 42, line 40, reads "-SO2-" should read -- -SO$_2$- --
Column 43, line 34, reads "indoyl." should read --indolyl.--
Column 43, line 40, reads ". . .-methenone." should read --. . .-methanone.--
Column 44, line 11, reads "compound of claim2" should read --compound of claim 1--
Column 44, line 30, reads "tetraliydroiso-" should read -- tetrahydroiso- --

Signed and Sealed this

Eighteenth Day of November, 2008

JON W. DUDAS
*Director of the United States Patent and Trademark Office*